(12) United States Patent
Kikuchi

(10) Patent No.: US 12,347,066 B2
(45) Date of Patent: Jul. 1, 2025

(54) INFORMATION PROCESSING SYSTEM, ENDOSCOPE SYSTEM, AND INFORMATION STORAGE MEDIUM

(71) Applicant: OLYMPUS CORPORATION, Tokyo (JP)

(72) Inventor: Sunao Kikuchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 506 days.

(21) Appl. No.: 17/731,627

(22) Filed: Apr. 28, 2022

(65) Prior Publication Data

US 2022/0253979 A1    Aug. 11, 2022

Related U.S. Application Data

(63) Continuation of application No. PCT/JP2019/043806, filed on Nov. 8, 2019.

(51) Int. Cl.
*G06T 3/4053* (2024.01)
*A61B 1/00* (2006.01)
*G06T 5/70* (2024.01)

(52) U.S. Cl.
CPC ...... *G06T 3/4053* (2013.01); *A61B 1/000096* (2022.02); *G06T 5/70* (2024.01);
(Continued)

(58) Field of Classification Search
CPC .................... G06T 3/4053; G06T 5/70; G06T 2207/10068; G06T 2207/20081;
(Continued)

(56) References Cited

U.S. PATENT DOCUMENTS

2006/0038891 A1\*  2/2006  Okutomi .............. H04N 23/843
                                                                 348/222.1
2017/0032501 A1\*  2/2017  Kusumi ................... G06T 5/73
(Continued)

FOREIGN PATENT DOCUMENTS

JP    2010-250774 A    11/2010
JP    2016-092596 A     5/2016
(Continued)

OTHER PUBLICATIONS

A New Deep Generative Network for Unsupervised Remote Sensing Single-Image Super-Resolution, by J. Haut, R. Fernandez-Beltran, M. Paoletti, J. Plaza, A. Plaza, F. Pla, IEEE Transactions on Geoscience and Remote Sensing (vol. 56, Issue: 11, 2018, pp. 6792-6810) pub Jun. 28, 2018 (Year: 2018).\*
(Continued)

*Primary Examiner* — Nancy Bitar
*Assistant Examiner* — Heath E. Wells
(74) *Attorney, Agent, or Firm* — Scully, Scott, Murphy & Presser, P.C.

(57) ABSTRACT

An information processing system includes a processor. The trained model is trained to resolution recover a low resolution training image generated by low resolution processing performed on a high resolution training image to a high resolution training image that represents a high resolution image captured with a predetermined object through the first imaging system. The low resolution processing represents processing that generates a low resolution image as if captured with the predetermined object through the second imaging system and processing that simulates the second imaging method, and includes processing that simulates a resolution characteristic of an optical system of the second imaging system. The processor uses the trained model to resolution recover the processing target image captured
(Continued)

through a second imaging system to an image having a resolution at which the first imaging system performs imaging.

16 Claims, 20 Drawing Sheets

(52) U.S. Cl.
CPC .............. *G06T 2207/10068* (2013.01); *G06T 2207/20081* (2013.01); *G06T 2207/20084* (2013.01)

(58) Field of Classification Search
CPC ... G06T 2207/20084; G06T 5/60; G06T 5/73; G06T 3/4046; A61B 1/000096; A61B 1/000095; H04N 23/13; H04N 23/555; H04N 23/951
USPC .......................................................... 382/156
See application file for complete search history.

(56) References Cited

U.S. PATENT DOCUMENTS

| | | | |
|---|---|---|---|
| 2018/0336662 A1 | 11/2018 | Kimura | |
| 2019/0087943 A1* | 3/2019 | Maalouf | G06T 5/10 |
| 2020/0285883 A1* | 9/2020 | Hiasa | G06F 18/2148 |
| 2021/0015346 A1* | 1/2021 | Kuroda | A61B 1/01 |
| 2022/0392617 A1* | 12/2022 | Asai | G16H 40/20 |

FOREIGN PATENT DOCUMENTS

| | | | |
|---|---|---|---|
| JP | 2016-100795 A | | 5/2016 |
| JP | 6236731 B1 | | 11/2017 |
| JP | 2018-005841 A | | 1/2018 |
| JP | 2018-195069 A | | 12/2018 |
| WO | WO-2024053046 A1 * | | 3/2024 |

OTHER PUBLICATIONS

International Search Report dated Jan. 21, 2020 received in PCT/JP2019/043806.

* cited by examiner

INFORMATION PROCESSING SYSTEM, ENDOSCOPE SYSTEM, AND INFORMATION STORAGE MEDIUM

CROSS REFERENCE TO RELATED APPLICATION

This application is a continuation of International Patent Application No. PCT/JP2019/043806, having an international filing date of Nov. 8, 2019, which designated the United States, the entirety of which is incorporated herein by reference.

BACKGROUND

Known is a super resolution technique of performing image processing to generate a high resolution image as if captured through a high resolution image sensor from an input image captured through a low resolution image sensor. Japanese Patent No. 6236731 discloses a technique of using a trained model obtained by deep learning to super resolve an input image. In a training stage, with a high resolution image actually captured through a high resolution image sensor serving as training data, the high resolution image is simply reduced, whereby a low resolution image corresponding to an input image when inference is made is generated. The low resolution image is entered to a training model, and deep learning is performed based on an output image output from the training model and the high resolution image serving as the training data.

SUMMARY

In accordance with one of some aspect, there is provided an information processing system comprising: a processor to use a trained model and to be entered a processing target image captured through a second imaging system that has a smaller number of pixels than pixels of a first imaging system including a first image sensor in a first imaging method, and that includes a second image sensor in a second imaging method different from the first imaging method, wherein the trained model represents a trained model trained to resolution recover a low resolution training image to a high resolution training image, the high resolution training image represents a high resolution image captured with a predetermined object through the first imaging system, the low resolution training image is generated by low resolution processing performed on the high resolution training image, the low resolution processing represents processing that generates a low resolution image as if captured with the predetermined object through the second imaging system and imaging method simulation processing that simulates the second imaging method, and includes optical system simulation processing that simulates a resolution characteristic of an optical system of the second imaging system, and the processor uses the trained model to resolution recover the processing target image to an image having a resolution at which the first imaging system performs imaging.

In accordance with one of some aspect, there is provided an endoscope system comprising: a processor unit including the above information processing system; and an endoscopic scope that is connected to the processor unit, that captures the processing target image, and that transmits the processing target image to the input device.

In accordance with one of some aspect, there is provided a non-transitory information storage medium that stores a trained model causing a computer to function to resolution recover a processing target image captured through a second imaging system that performs imaging at a lower resolution than a resolution at which a first imaging system performs imaging to the resolution at which the first imaging system performs imaging, wherein the trained model is trained to resolution recover a low resolution training image to a high resolution training image, the high resolution training image represents a high resolution image captured with a predetermined object through the first imaging system including a first image sensor in a first imaging method, the low resolution training image is generated by low resolution processing that reduces a resolution of the high resolution training image, and the low resolution processing represents processing that generates a low resolution image as if captured with the predetermined object through the second imaging system that has a small number of pixels and that includes a second image sensor in a second imaging method different from the first imaging method, and imaging method simulation processing that simulates the second imaging method, and includes optical system simulation processing that simulates a resolution characteristic of an optical system of the second imaging system.

DESCRIPTION OF EXEMPLARY EMBODIMENTS

Figure 1:
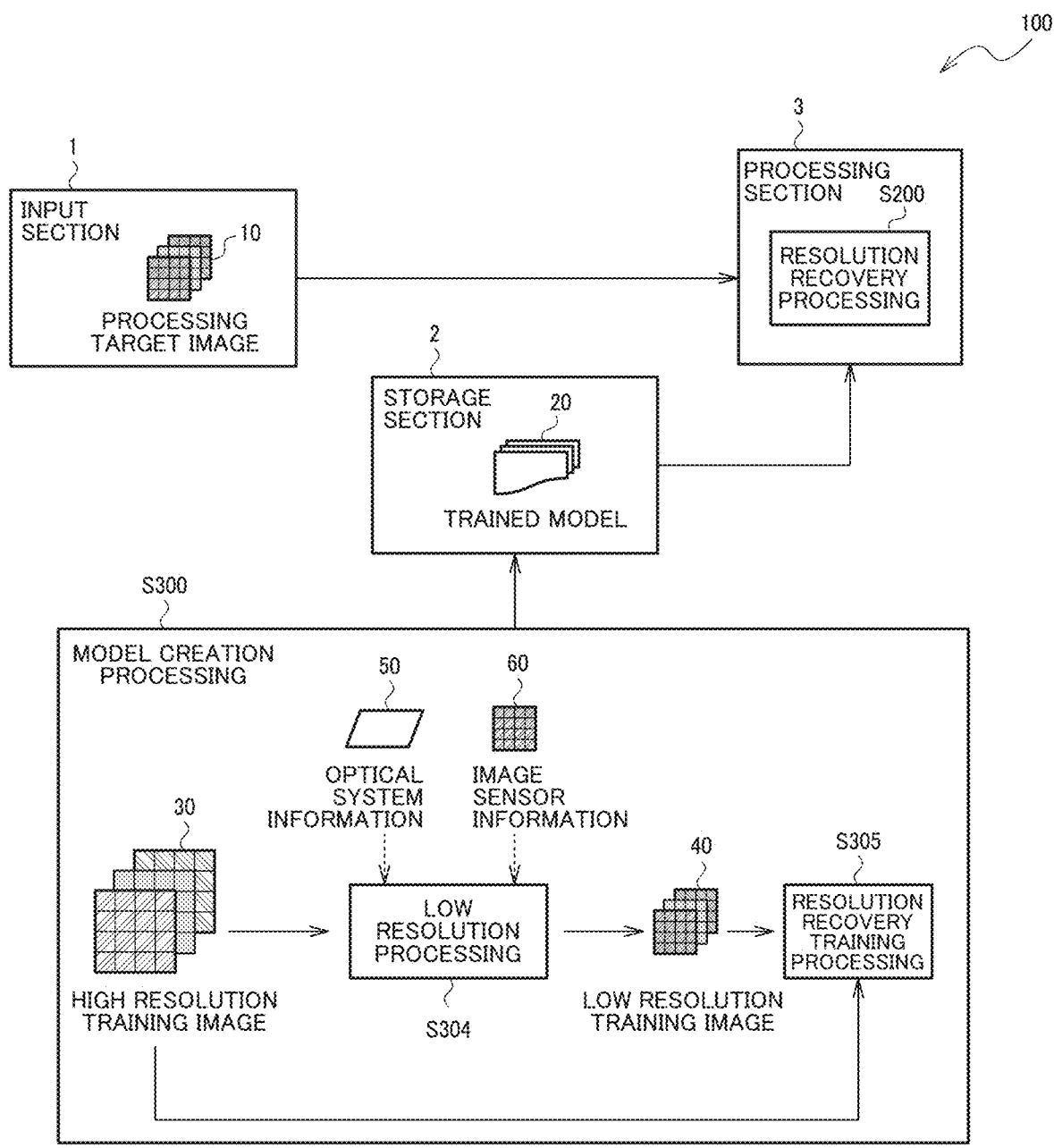
FIG. 1 illustrates a configuration example of an information processing system in accordance with a first embodiment and a processing flow of model creation processing.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

The following description will be given using an example of a case of applying an information processing system to a medical endoscope, but application is not limited thereto, and the information processing system in accordance with the present disclosure can be applied to various kinds of imaging systems or various kinds of video display systems. For example, the information processing system in accordance with the present disclosure can be applied to a still camera, a video camera, a television receiver, a microscope, or an industrial endoscope.

1. First Embodiment

As described above, in super resolution using machine learning, there is an issue that accuracy of super resolution decreases unless an appropriate low resolution image can be generated. This issue is now described using an example of an endoscope system.

An endoscope is advantageous in that less-invasive inspection can be performed on a patient as a probe diameter becomes smaller. An example of an endoscope having a small probe diameter is a transnasal endoscope. Meanwhile, since a size of an imager becomes smaller as the probe diameter becomes smaller, a resolution decreases. Hence, it can be assumed to use a super resolution technique, which is one type of image processing, to increase a resolution of the transnasal endoscope, and thereby generate an image as if captured through an endoscope having a large probe diameter.

As discussed in Japanese Patent No. 6236731 described above, in recent years, a method using deep learning has enabled highly accurate processing in the super resolution technique for generating a high resolution color image from a low resolution color image. In the deep learning, a set of a high resolution image and a low resolution image is necessary to determine a parameter for resolution recovery. Since it is difficult in terms of quantity and quality to capture and obtain each of the high resolution image and low resolution image, a method of simply reducing a resolution of the high resolution image through a method such as bicubic interpolation to generate the low resolution image is used in many cases.

Also, in a case where a super resolution is applied to an endoscope image, it is difficult to capture a large amount of high resolution images and low resolution images in the body cavity without displacement. Thus, processing of generating the low resolution image from the high resolution image is necessary. However, in image reduction processing using the bicubic interpolation or the like, an imaging system that actually captures endoscope images is not taken into consideration. Thus, a sense of resolution of the low resolution image obtained by the image reduction processing is different from a sense of resolution of the endoscope image. For this reason, there is an issue that a highly accurate super resolution image cannot be recovered from an image captured through a low resolution imager, such as a small imager.

FIG. 1 illustrates a configuration example of an information processing system 100 in accordance with a first embodiment and a processing flow of model creation processing S300. The information processing system 100 includes an input section 1 that enters a processing target image 10 to a processing section 3, a storage section 2 that stores a trained model 20, and a processing section 3 that performs resolution recovery processing. Note that the input section 1, the storage section 2, and the processing section 3 are also referred to as an input device, a storage device, and a processing device, respectively.

The information processing system 100 is a system that performs inference using the trained model 20. The inference in the present embodiment is processing of resolution recovering a high resolution image from the processing target image 10. The trained model 20 is generated by the model creation processing S300, and stored in the storage section 2. The model creation processing S300 is executed by, for example, a training device that is different from the information processing system 100. Alternatively, the information processing system 100 may execute the model creation processing S300 in a training stage, and make inference using the trained model 20 in an inference stage. In this case, the information processing system 100 also serves as the training device, and for example, the processing section 3 executes training processing.

A configuration of the information processing system 100 will be described first, and thereafter the flow of inference processing and the flow of training processing will be described.

The input section 1 is, for example, an image data interface that receives image data from an imaging system, a storage interface that reads out image data from a storage, a communication interface that receives image data from the outside of the information processing system 100, or the like. The input section 1 enters the acquired image data as the processing target image 10 to the processing section 3. In a case where the input section 1 acquires a movie, the input section 1 enters a frame image of the movie as the processing target image 10 to the processing section 3.

The storage section 2 is a storage device, and is, for example, a semiconductor memory, a hard disk drive, an optical disk drive, or the like. The trained model 20 generated by the model creation processing S300 is preliminarily stored in the storage section 2. Alternatively, the trained model 20 may be entered to the information processing system 100 from an external device such as a server via a network, and stored in the storage section 2.

The processing section 3 uses the trained model 20 stored in the storage section 2 to perform the resolution recovery processing S200 on the processing target image 10, and thereby recovers the high resolution image from the processing target image 10. The recovered high resolution image is an image in which an object identical to that of the processing target image 10 is seen, and is an image at a higher resolution than a resolution of the processing target image 10. The resolution is an index indicating how finely the object seen in the image is resolved. The resolution depends on, for example, the number of pixels of an image, performance of an optical system used for imaging, a type of an image sensor used for imaging, a content of image processing performed on the image, and the like.

Assume that an imaging system that performs imaging at a resolution serving as a target of resolution recovery is a first imaging system. The processing target image 10 is captured through a second imaging system that performs imaging at a lower resolution than the resolution at which the first imaging system performs imaging. The high resolution image recovered from the processing target image 10 corresponds to an image as if captured with an object identical to that of the processing target image 10 captured through the first imaging system. The imaging system includes an optical system that forms an image of the object and an image sensor that performs imaging of the object whose image is formed by the optical system. The image sensor is also called as an imager. Various types such as a monochrome type, a Bayer type, and a complementary color type can be adopted to the image sensor. For example, the first imaging system is an imaging system of a first endoscope provided with a scope having a large diameter, and the second imaging system is an imaging system of a second endoscope provided with a scope having a diameter smaller than that of the scope of the first endoscope.

Hardware that constitutes the processing section 3 is, for example, a general-purpose processor, such as a central processing unit (CPU). In this case, the storage section 2 stores, as the trained model 20, a program in which an inference algorithm is described, and a parameter used for the inference algorithm. Alternatively, the processing section 3 may be a dedicated processor that implements the inference algorithm as hardware. The dedicated processor is, for example, an application-specific integrated circuit (ASIC), a field-programmable gate array (FPGA), or the like. In this case, the storage section 2 stores a parameter used for the inference algorithm as the trained model 20.

A neural network can be applied as the inference algorithm. A weight coefficient assigned between connected nodes in the neural network is the parameter. The neural network includes an input layer that takes input image data, an intermediate layer that executes calculation processing on data input via the input layer, and an output layer that outputs image data based on a calculation result output from the intermediate layer. A convolutional neural network (CNN) is preferable as the neural network used for the resolution recovery processing S200. However, the neural network is not limited to the CNN, and various kinds of artificial intelligence (AI) techniques can be adopted.

Figure 2:
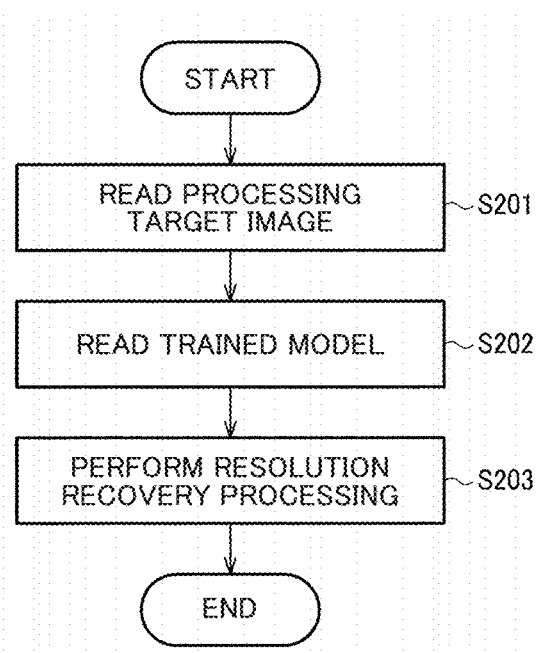
FIG. 2 illustrates a processing flow of resolution recovery processing.

FIG. 2 illustrates the processing flow of the resolution recovery processing S200.

In step S201, the processing section 3 reads the processing target image 10 from the input section 1. In step S202, the processing section 3 reads the trained model 20 used for resolution recovery from the storage section 2. In step S203, the processing section 3 uses the trained model 20 acquired in step S202 to perform resolution recovery processing on the processing target image 10 acquired in step S201, and generates a high resolution image. Note that the order of S201 and S202 may be exchanged.

Figure 3:
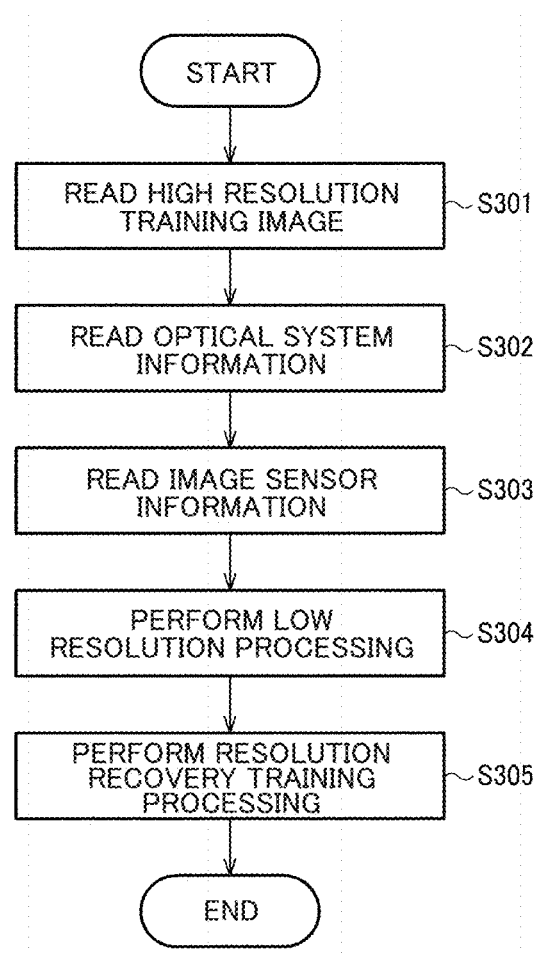
FIG. 3 illustrates a processing flow of the model creation processing.

FIG. 3 illustrates a processing flow of the model creation processing S300. The training device includes a processing section that executes the model creation processing S300. The processing section is hereinafter referred to as a training processing section.

In step S301, the training processing section reads a high resolution training image 30. The high resolution training image 30 is an image captured through the above-mentioned first imaging system. In steps S302 and S303, the training processing section reads optical system information 50 and image sensor information 60 used when generating a low resolution training image 40. The optical system information 50 is information regarding a resolution of an optical system included in each of the first imaging system and the second imaging system. The image sensor information 60 is information regarding a resolution of an image sensor included in each of the first imaging system and the second imaging system.

In step S304, the training processing section uses at least one of the optical system information acquired in step S302 or the image sensor information acquired in step S303 to perform low resolution processing on the high resolution training image 30 acquired in step S301, and generates the low resolution training image 40. The low resolution training image 40 corresponds to an image as if captured with an object identical to that of the high resolution training image 30 through the second imaging system, and has the number of pixels identical to that of the processing target image 10 when inference is performed.

In step S305, the training processing section uses the high resolution training image 30 acquired in step S301 and the low resolution training image 40 acquired in step S304 to perform resolution recovery training processing on the training model. The training processing section uses a plurality of high resolution training images 30 to repeatedly execute training processing in steps S301 to S305, and outputs the training model after training as the trained model 20. The training model used for the training processing has an algorithm identical to that of the trained model 20 used for inference. Specifically, the training model is a CNN, and the training processing section calculates a weight value and bias value of each layer of the CNN, and stores these values as the trained model 20.

Note that various kinds of known training algorithms can be adopted as an algorithm for machine learning in the neural network. For example, a supervised training algorithm using a backpropagation method can be adopted.

Figure 4:
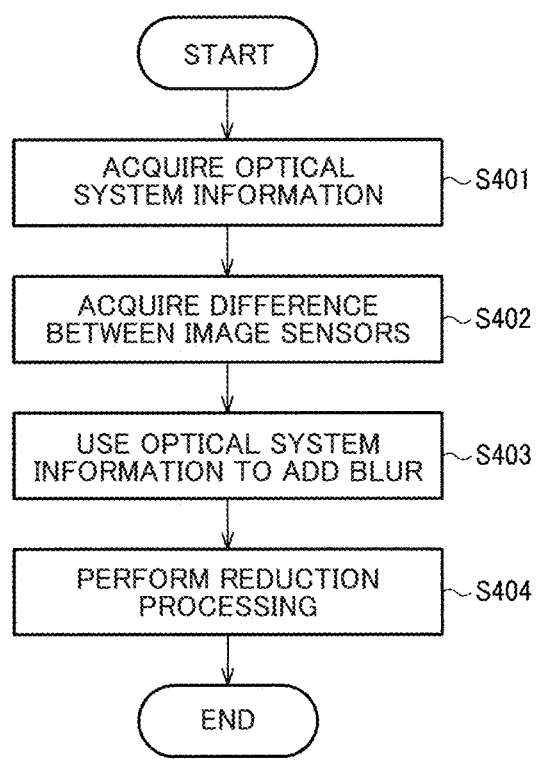
FIG. 4 illustrates a processing flow of low resolution processing.

FIG. 4 illustrates the processing flow of the low resolution processing S304. In FIG. 4, the training processing section uses the optical system information 50 and the image sensor information 60 to generate the low resolution training image 40 from the high resolution training image 30.

In step S401, the training processing section acquires the optical system information 50 when acquiring the high resolution training image 30 and the optical system information 50 used for the low resolution training image 40. The optical system information 50 mentioned herein represents a focal length and aperture stop of the optical system. The training processing section acquires a point spread function (PSF) or an optical transfer function (OTF) under these conditions. That is, the training processing section acquires the PSF of the first imaging system and the PSF of the second imaging system, or the OTF of the first imaging system and the OTF of the second imaging system.

In step S402, the training processing section uses information such as the number of pixels of the high resolution training image 30, the number of pixels of the low resolution training image 40, and an imaging method to set a reduction ratio of the low resolution training image 40 with respect to the high resolution training image 30. For example, in a case where the high resolution training image 30 has 640×480 [pixels] and the low resolution training image 40 has 320×240 [pixels], the reduction ratio is 1/2 both lengthwise and widthwise. Note that the order of S401 and S402 may be exchanged.

In step S403, the training processing section uses the optical system information calculated in step S401 to add a blur to the high resolution training image 30. For example, the optical system of the second imaging system that supports the low resolution training image 40 is inferior in performance to the optical system of the first imaging system that acquires the high resolution training image 30. To prevent aliasing or the like, processing of preliminarily removing a high frequency band of the image using a bicubic filter or the like is typically performed. Although this makes a band of the reduced image smaller than the band of the image before the reduction, performing only this processing cannot reproduce a difference in bands in a case where optical systems are different. To address this, a blur is added to the image to complement a difference between the optical systems. The training processing section uses the PSFs of the first and second imaging systems or the OTFs of the first and second imaging systems, the PSFs or the OTFs being acquired in step S401, to complement the difference so that a blur in the high resolution training image is similar to a blur of the image captured through the second imaging system. Note that details of the blur processing will be described later.

In step S404, the training processing section performs reduction processing on the image generated in step S403 with the reduction ratio calculated in step S402. For example, the training processing section performs reduction processing of bicubic interpolation, bilinear interpolation, or the like. The training processing section executes the resolution recovery training processing in step S305 with the image subjected to the reduction processing serving as the low resolution training image 40. Note that the order of the blur processing in step S403 and the reduction processing in step S404 may be reversed. That is, the training processing section may perform the reduction processing on the high resolution training image 30 and the blur processing on the image subjected to the reduction processing to generate the low resolution training image 40.

In accordance with the present embodiment, the trained model 20 is trained so as to resolution recover the low resolution training image 40 into the high resolution training image 30. The high resolution training image 30 is a high resolution image captured with a predetermined object through the first imaging system. The low resolution processing is performed on the high resolution training image 30 to generate the low resolution training image 40. The low resolution processing represents processing to generate a low resolution image as if captured with the predetermined object through the second imaging system. As described in S401 to S403 in FIG. 4, the low resolution processing includes optical system simulation processing that simulates a resolution characteristic of the optical system of the second imaging system. The optical system simulation processing is, for example, processing of performing convolution calculation of PSFs on the high resolution training image 30 so as to complement a difference between the PSF of the optical system of the first imaging system and the PSF of the optical system of the second imaging system.

This enables highly accurate resolution recovery of an image as if captured through the first imaging system from the processing target image 10 captured through the second imaging system. That is, since the resolution characteristic of the optical system is taken into consideration at the time of reducing the resolution of the high resolution training image 30 into the resolution of the low resolution training image 40, it is possible to generate the low resolution training image 40 having the resolution that is equal to the resolution of the processing target image 10 captured through the first imaging system. Using the low resolution training image 40 to perform training of a recovery parameter enables implementation of high-performance super resolution processing.

The blur processing in step S403 is now described. As an example of the blur processing, first and second methods are described.

Figure 20:
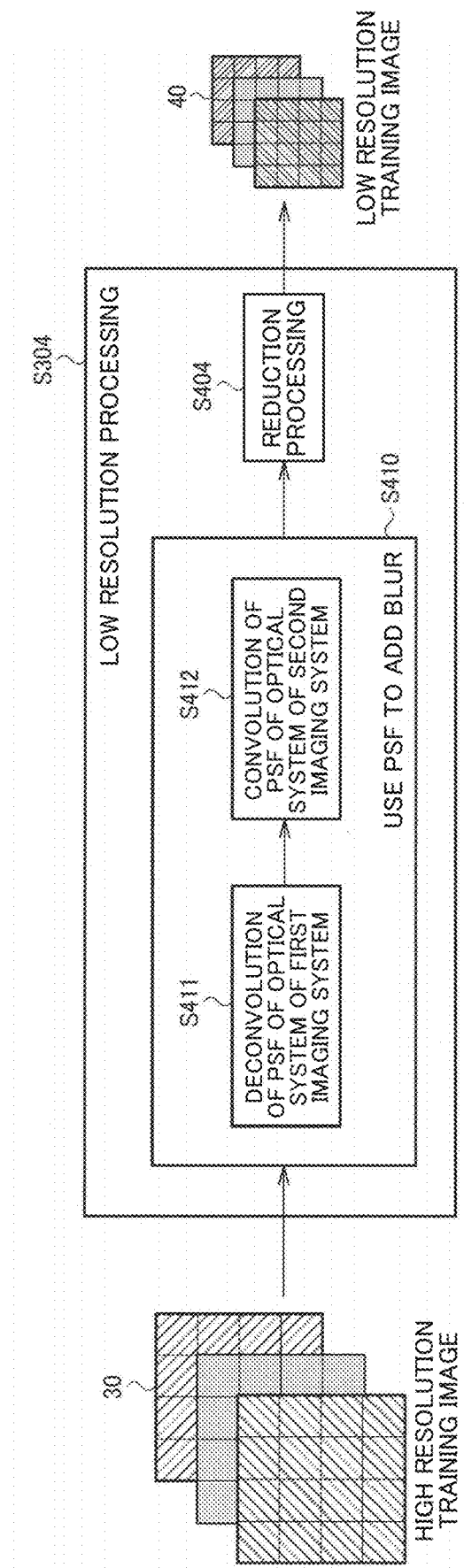
FIG. 20 illustrates a processing flow of blur processing using a first method.

FIG. 20 illustrates a processing flow of the blur processing using the first method. As described in step S410, the training processing section uses the PSF of the first imaging system that performs imaging at a high resolution and the PSF of the second imaging system that performs imaging at a low resolution to add a blur to the high resolution training image 30. The PSF is a function representing a unit impulse response to the optical system, i.e., a function representing image distribution when the optical system uses a point light source to form an image. As described in step S404, the training processing section performs reduction processing on the image obtained in step S410 and outputs a result of the processing as the low resolution training image 40.

Details of step S410 are now described. As described in step S411, the training processing section performs deconvolution of the PSF of the first imaging system on the high resolution training image 30. As described in step S412, the training processing section performs convolution of the PSF of the second imaging system on the high resolution training image 30. Specifically, the training processing section adds the blur using the following Expression (1). In the following Expression (1), $h_1$ and $h_2$ represent the PSF of the optical system of the first imaging system and the PSF of the optical system of the second imaging system, respectively, the PSFs being acquired in step S401, f represents the high resolution training image 30, g represents an image to which the blur is added, n is a noise clause, and * represents convolution calculation. Note that the noise clause n may be omitted.

[Expression 1]

$$g = h_2 * h_1^{-1} * f + n \qquad (1)$$

Figure 21:
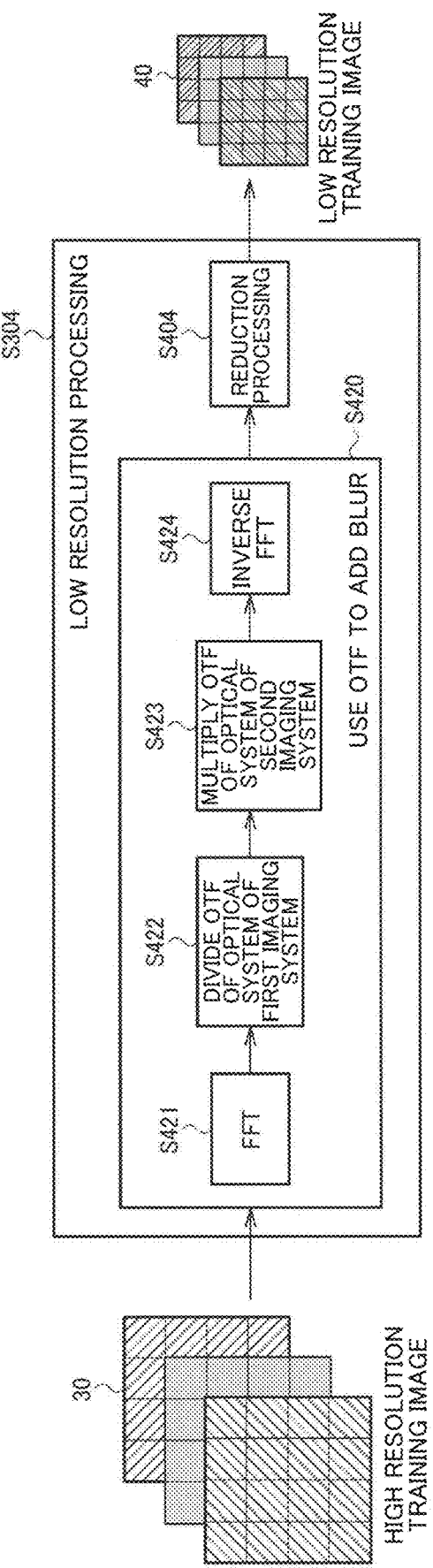
FIG. 21 illustrates a processing flow of blur processing using a second method.

FIG. 21 illustrates a processing flow of blur processing using the second method. As described in step S420, the training processing section uses the OTF of the optical system of the high resolution first imaging system and the OTF of the optical system of the low resolution second imaging system to add the blur to the high resolution training image 30. The OTF is a function representing a unit impulse frequency response to the optical system, i.e., a function representing a frequency characteristic of image distribution when the optical system uses the point light source to form an image. As described in step S404, the training processing section performs reduction processing on the image obtained in step S420 and outputs a result of the processing as the low resolution training image 40.

Details of step S420 are now described. The training processing section reads the OTF of the optical system of the first imaging system and the OTF of the optical system of the second imaging system as the optical system information 50 in FIG. 1. As described in step S421 in FIG. 21, the training processing section performs FFT (Fast Fourier Transform) on the high resolution training image to obtain the frequency characteristic of the high resolution training image 30. In steps S422 and S423, the training processing section calculates a result of dividing the frequency characteristic of the high resolution training image 30 by the OTF of the first imaging system and multiplying a result of the division by the OTF of the second imaging system. In step S424, the training processing section performs reverse FFT on the frequency characteristic as the calculation result.

In accordance with the present embodiment, performing the blur processing using the OTF enables calculation substantially similar to the first method using the PSF. Specifically, the OTF and the PSF have a Fourier transformation relationship as indicated by the following Expression (2). That is, a frequency response of the OTF is matched with the unit impulse response (PSF) of the optical system in a physical space. For this reason, performing the blur processing that uses the OTF described in step S420 in FIG. 21 enables obtaining of a result substantially similar to that of the blur processing that uses the PSF described in step S410 in FIG. 20.

[Expression 2]

$$OTF(fx,fy) = \iint PSF(x,y) e^{-i2\pi(fx \times x + fy \times y)} dx dy \quad (2)$$

Note the that in the above-mentioned embodiment, the resolution characteristic of the optical system of the second imaging system is simulated using a transfer function such as the PSF and the OTF, but the simulation is not limited thereto, and the resolution characteristic of the optical system of the second imaging system may be simulated using calculation based on a design value of a known optical system or machine learning.

2. Second Embodiment

In the second embodiment, the second imaging system includes a simultaneous-type image sensor, and performs the low resolution processing in consideration of the type of the image sensor. Specifically, a processing target image is captured through an image sensor having a Bayer array, and the low resolution processing in consideration of decrease in resolution by demosaicing processing is performed. The following description will be given using an example of the Bayer-type image sensor, but the simultaneous-type image sensor is not limited to the Bayer-type image sensor. Note that a description of a configuration and processing similar to those in the first embodiment is omitted.

Figure 5:
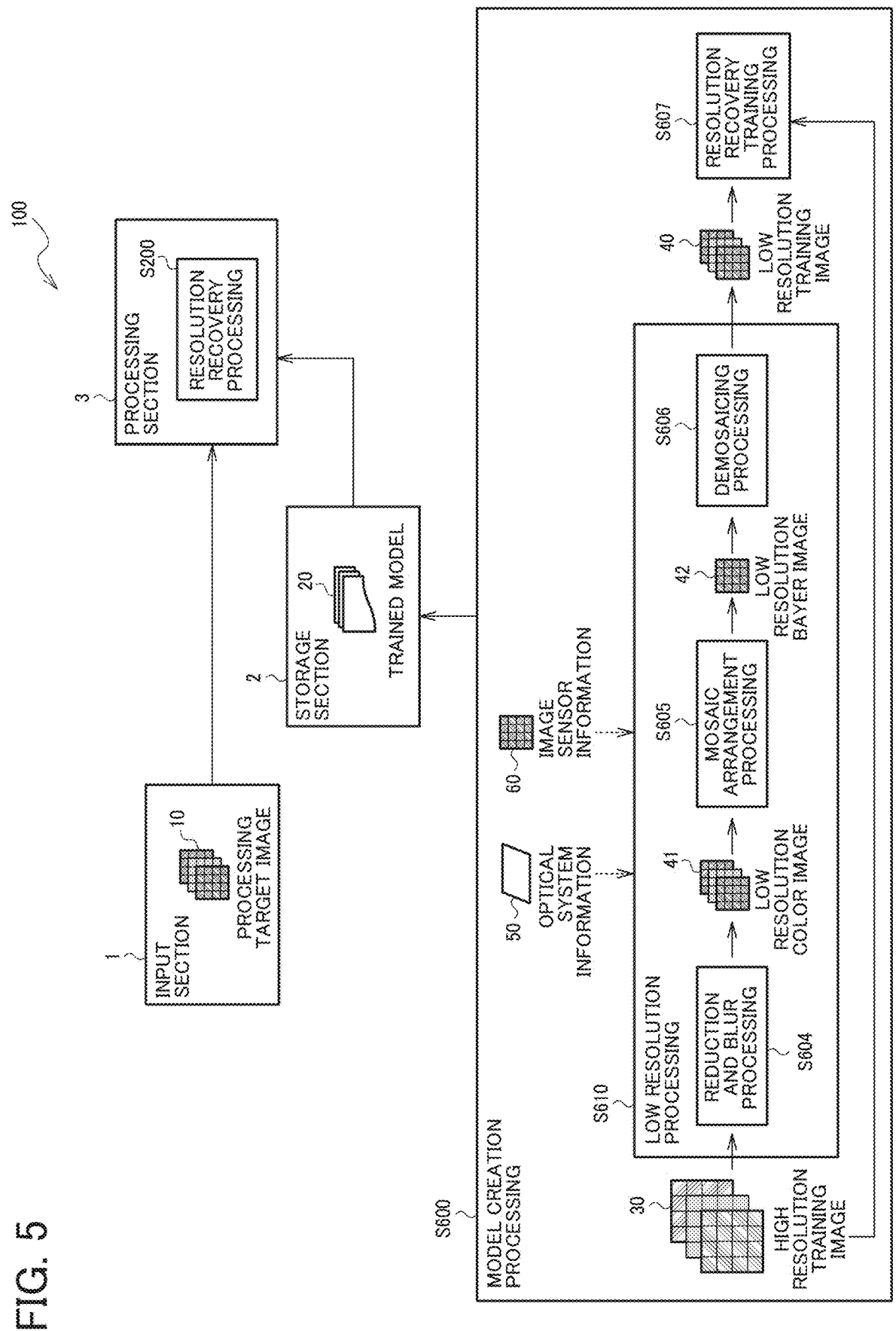
FIG. 5 illustrates a configuration example of an information processing system in accordance with a second embodiment and a processing flow of model creation processing.

FIG. 5 illustrates a configuration example of the information processing system 100 in accordance with a second embodiment and a processing flow of model creation processing S600. The configuration and resolution recovery processing of the information processing system 100 are similar to those of the first embodiment illustrated in FIGS. 1 and 2.

Figure 6:
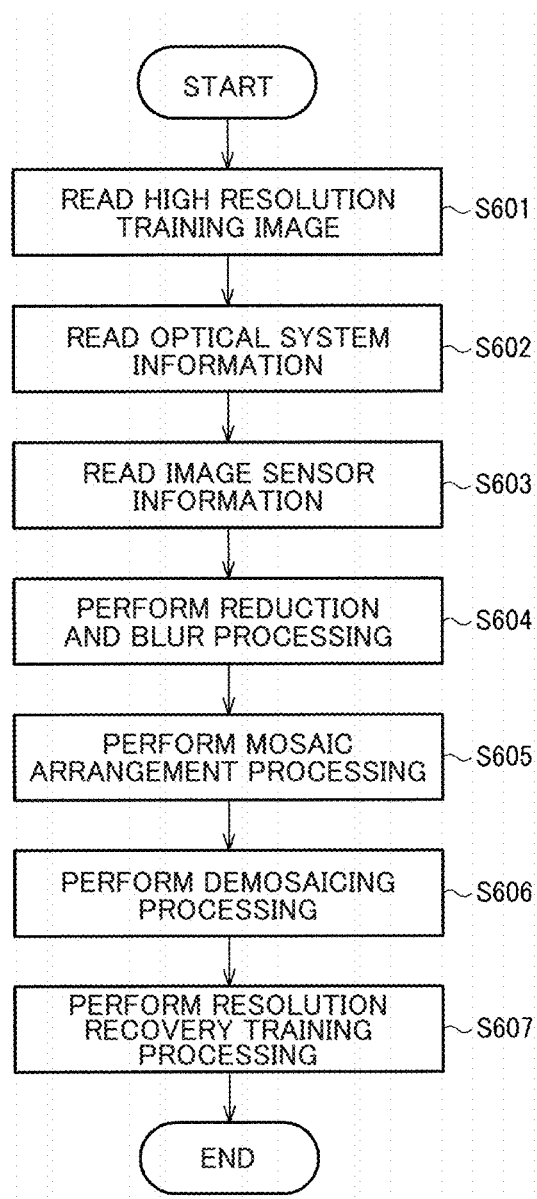
FIG. 6 illustrates a processing flow of model creation processing.

FIG. 6 illustrates a processing flow of the model creation processing S600. Steps S601 to S603 are identical to steps S301 to S303 of the first embodiment.

Steps S604 to S606 correspond to the low resolution processing described in step S610 described in FIG. 5. The reduction and blur processing in step S604 corresponds to steps S401 to S404 of the first embodiment described in FIG. 4. That is, in step S604, the training processing section uses the optical system information to add the blur to the high resolution training image 30, and uses image sensor information to perform reduction processing on the image to which the blur is added. The image subjected to the reduction processing is a low resolution color image 41 in which red, green, and blue (RGB) pixel values exist in each pixel.

In step S605, the training processing section performs mosaic arrangement processing on the low resolution color image 41 generated in step S604. That is, the training processing section uses the image sensor information 60 acquired in step S603 to perform mosaic arrangement of pixel values of the low resolution color image 41 in a Bayer pattern, and thereby generates a low resolution Bayer image 42. Any one color of RGB is allocated to each pixel of the low resolution Bayer image 42. Taking an R pixel of the low resolution Bayer image 42 for example, the training processing section extracts an R pixel value from pixels of the low resolution color image 41 at a position identical to that of the R pixel, and allocates the R pixel value to the R pixel of the low resolution Bayer image 42. The same applies to G and B pixels of the low resolution Bayer image 42.

In step S606, the training processing section performs demosaicing processing on the low resolution Bayer image 42 in a mosaic pattern to make the low resolution Bayer image 42 a color image again. The image after the demosaicing processing serves as the low resolution training image 40. For example, as the demosaicing processing, existing processing such as interpolation using a color correlation or bilinear interpolation can be adopted. In a case where the demosaicing processing is known at the time of generation of the processing target image 10, it is desirable to perform processing similar to the demosaicing processing in step S606.

In step S607, similarly to step S305 of the first embodiment, the training processing section uses the high resolution training image 30 acquired in step S601 and the low resolution training image 40 acquired in step S606 to perform resolution recovery training processing to generate the trained model 20.

In accordance with the present embodiment, the first imaging system includes a first image sensor in a first imaging method. The second imaging system includes a second image sensor that has a smaller number of pixels than pixels of the first image sensor and that is in a second imaging method different from the first imaging method. The low resolution processing S610 further includes imaging method simulation processing that simulates the second imaging method. The imaging method simulation processing simulates image processing when the processing target image 10 is generated from image signals acquired by the second image sensor. For example, the imaging method simulation processing is the mosaic arrangement processing S605 and the demosaicing processing S606, as illustrated in FIGS. 5 and 6.

Image processing when a color image is generated from image signals acquired by an image sensor is different depending on an imaging method. The image processing affects a sense of resolution of the color image. In accordance with the present embodiment, performing the imaging method simulation processing in the low resolution processing S610 enables reproduction of the sense of resolution of the processing target image 10 on the low resolution training image 40. This can implement a high-performance super resolution.

In accordance with the present embodiment, the low resolution processing S610 represents processing of performing reduction processing on the high resolution training image 30 conforming to the first imaging method, and performing the imaging method simulation processing on the image 41 subjected to the reduction processing. The imaging method simulation processing represents processing of generating the image 42 conforming to the second imaging method from the image 41 subjected to the reduction processing (S605), performing image processing identical to the image processing performed when the processing target image 10 is generated (S606) to the generated image 42 conforming to the second imaging method, and thereby generating the low resolution training image 40.

With this processing, the image 42 conforming to the second imaging method is generated once from the high resolution training image 30, thereafter the image processing identical to the image processing performed when the processing target image 10 is generated is performed on the image 42. This enables simulation of the image processing performed when the processing target image 10 is generated from an image signal acquired by the second image sensor.

Additionally, in the present embodiment, in a case where light having a plurality of wavelength bands is sequentially emitted, the first imaging system causes a monochrome image sensor to perform imaging at a timing when light of each wavelength band is emitted, thereby acquires a plurality of images. The high resolution training image 30 is a field sequential image obtained by combining a plurality of images. The second imaging system has a plurality of pixels having mutually different colors, and uses a synchronous-type image sensor in which one color is allocated to each pixel to acquire a Bayer image in which one color is allocated to each pixel. The low resolution processing S610 represents processing of reducing the number of pixels of the field sequential image (30), and performing the imaging method simulation processing on the image 41 subjected to the reduction processing. The imaging method simulation processing forms the low resolution Bayer image 42 from the image 41 subjected to the reduction processing (S605). The low resolution Bayer image 42 corresponds to the Bayer image acquired by the second imaging system. Subsequently, in the imaging method simulation processing, demosaicing processing is performed on the low resolution Bayer image 42 (S606), whereby the low resolution training image 40 is generated.

Specifically, the second image sensor has a plurality of types of pixels having mutually different spectral sensitivity characteristics. The high resolution training image 30 is the field sequential image generated by using the monochrome image sensor to combine imaging signals generated from light having a plurality of wavelength bands acquired by sequentially emitting light having the plurality of wavelength bands. The low resolution training image 40 is obtained by simulating an image captured through the second imaging system including the simultaneous-type image sensor that has a plurality of types of pixels having mutually different spectral sensitivities. The low resolution processing S610 represents processing of, at the time of simulation of the second imaging method, generating a signal of each pixel included in the simultaneous-type image sensor based on a signal generated from light having at least one wavelength band, out of signals generated from light having the plurality of wavelength bands acquired by the pixels of the monochrome image sensor at positions corresponding to the respective pixels, and thereafter performing the demosaicing processing (S606), and thereby generating the low resolution training image 40.

With this processing, in a case where the first imaging system is in a field sequential method and the second imaging system is in a simultaneous method, the simultaneous method serving as the second imaging method can be simulated in the low resolution processing. The demosaicing processing in the simultaneous method affects the sense of resolution of the processing target image 10. In accordance with the present embodiment, performing the demosaicing processing in the imaging method simulation processing enables reproduction of the sense of resolution of the processing target image 10 on the low resolution training image 40. This can implement a high-performance super resolution.

A modification of the second embodiment is now described. In the modification, low resolution processing in consideration of decrease in resolution due to noise reduction processing is performed in addition to the training processing in the second embodiment. Note that a description of a configuration and processing similar to those in the first and second embodiments is omitted.

Figure 7:
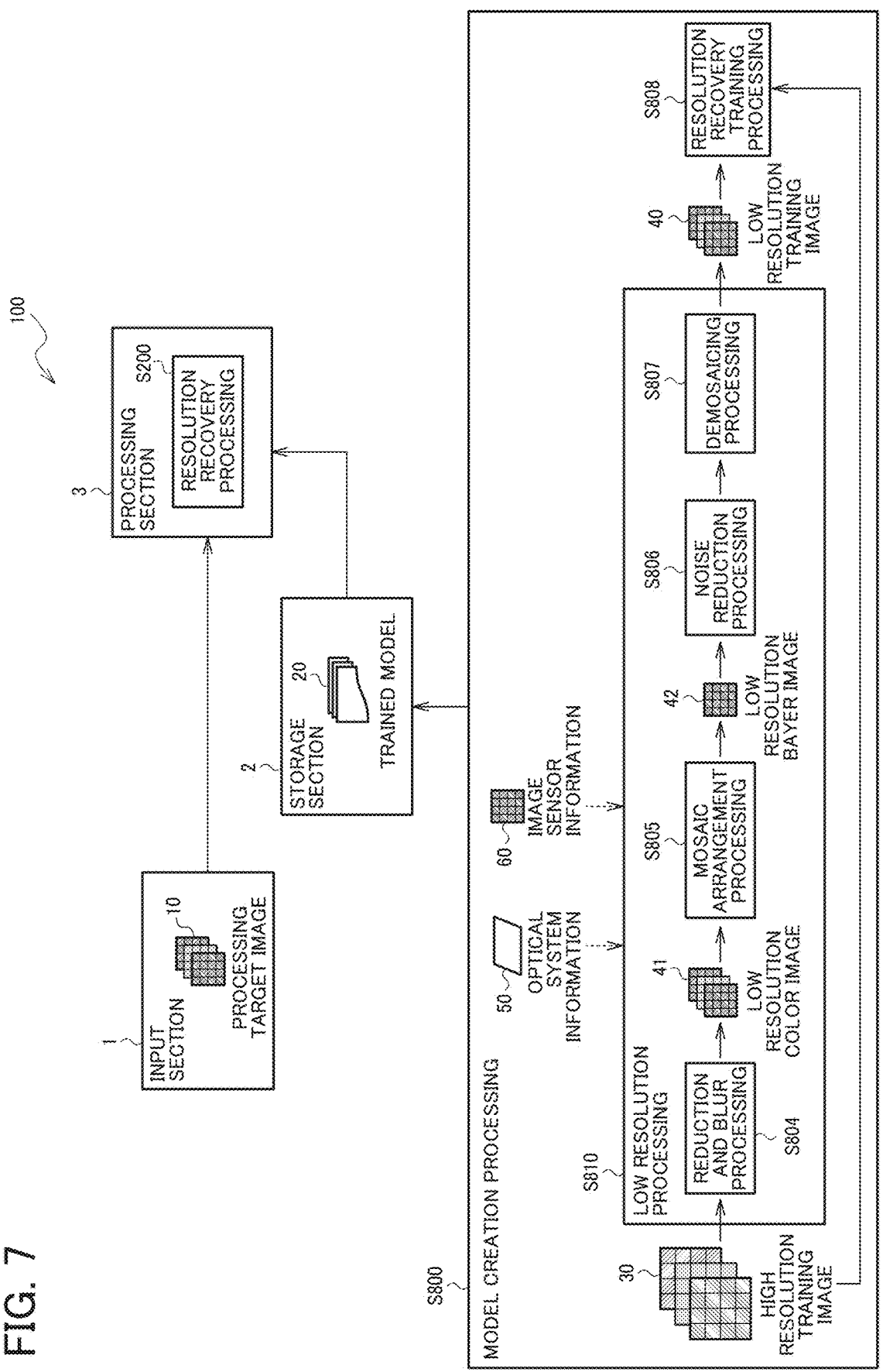
FIG. 7 illustrates a configuration example of an information processing system in accordance with a modification of the second embodiment and a processing flow of model creation processing.

FIG. 7 illustrates a configuration example of the information processing system 100 in accordance with the modification of the second embodiment and a processing flow of model creation processing S800. The configuration and resolution recovery processing of the information processing system 100 are similar to those of the first embodiment illustrated in FIGS. 1 and 2.

Figure 8:
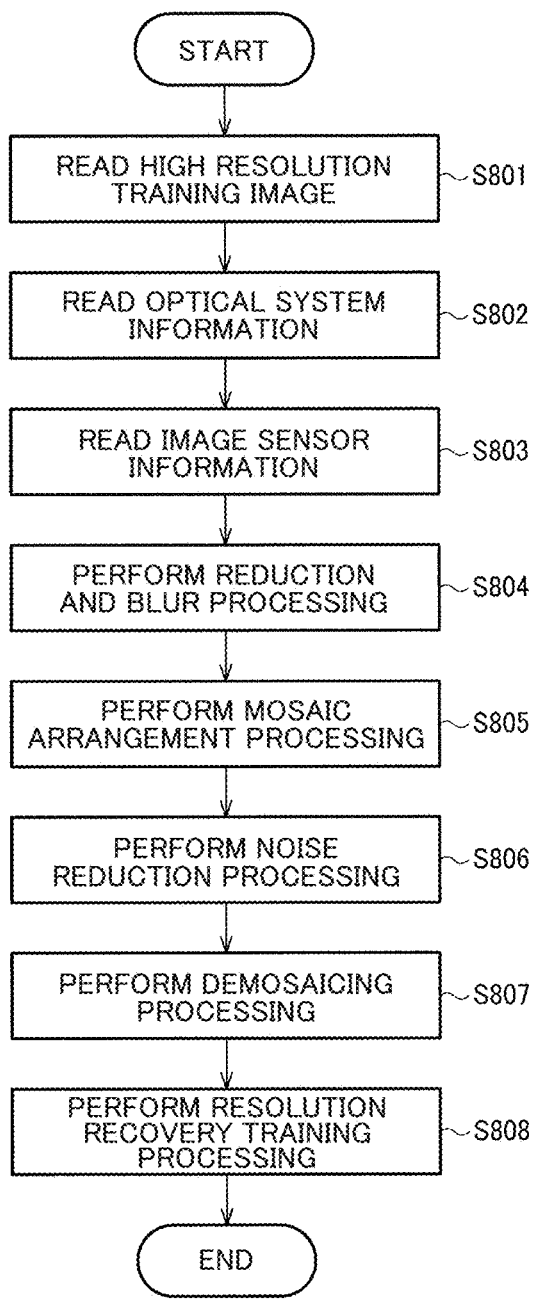
FIG. 8 illustrates a processing flow of model creation processing.

FIG. 8 illustrates a processing flow of the model creation processing S800. The low resolution processing in step S810 includes steps S804 to S807. Steps S801 to S805 are identical to steps S601 to S605 in the second embodiment.

In step S806, the training processing section performs noise reduction processing on the mosaic pattern low resolution Bayer image 42 generated in step S805. For example, known noise reduction processing on a Bayer image can be adopted. In step S807, similarly to step S606 in the second embodiment, the training processing section performs demosaicing processing on the image subjected to the noise reduction processing to generate the low resolution training image 40. In step S808, similarly to step S305 in the first embodiment, the training processing section uses the high resolution training image 30 acquired in step S801 and the low resolution training image 40 acquired in step S807 to perform resolution recovery training processing, and thereby generates the trained model 20.

In accordance with the present embodiment, the imaging method simulation processing further includes noise reduction processing on the low resolution Bayer image 42 (S806).

The noise reduction processing affects the sense of resolution of the processing target image 10. In accordance with the present embodiment, performing the noise reduction processing in the imaging method simulation processing enables reproduction of the sense of resolution of the processing target image 10 on the low resolution training image 40. This can implement a high-performance super resolution.

3. Third Embodiment

In a third embodiment, a type of an imaging system that captures the processing target image is detected, and resolution recovery corresponding to a result of the detection is performed. The following description will be given using an example of a case where an imaging method is different depending on the type of the imaging system, but a configuration is not limited thereto, and a resolution of the processing target image is only required to be different depending on the type of the imaging system. For example, the number of pixels, an optical system, or the like may be different depending on the type of the imaging system. Note that a description of a configuration and processing similar to those in the first and second embodiments is omitted.

Figure 9:
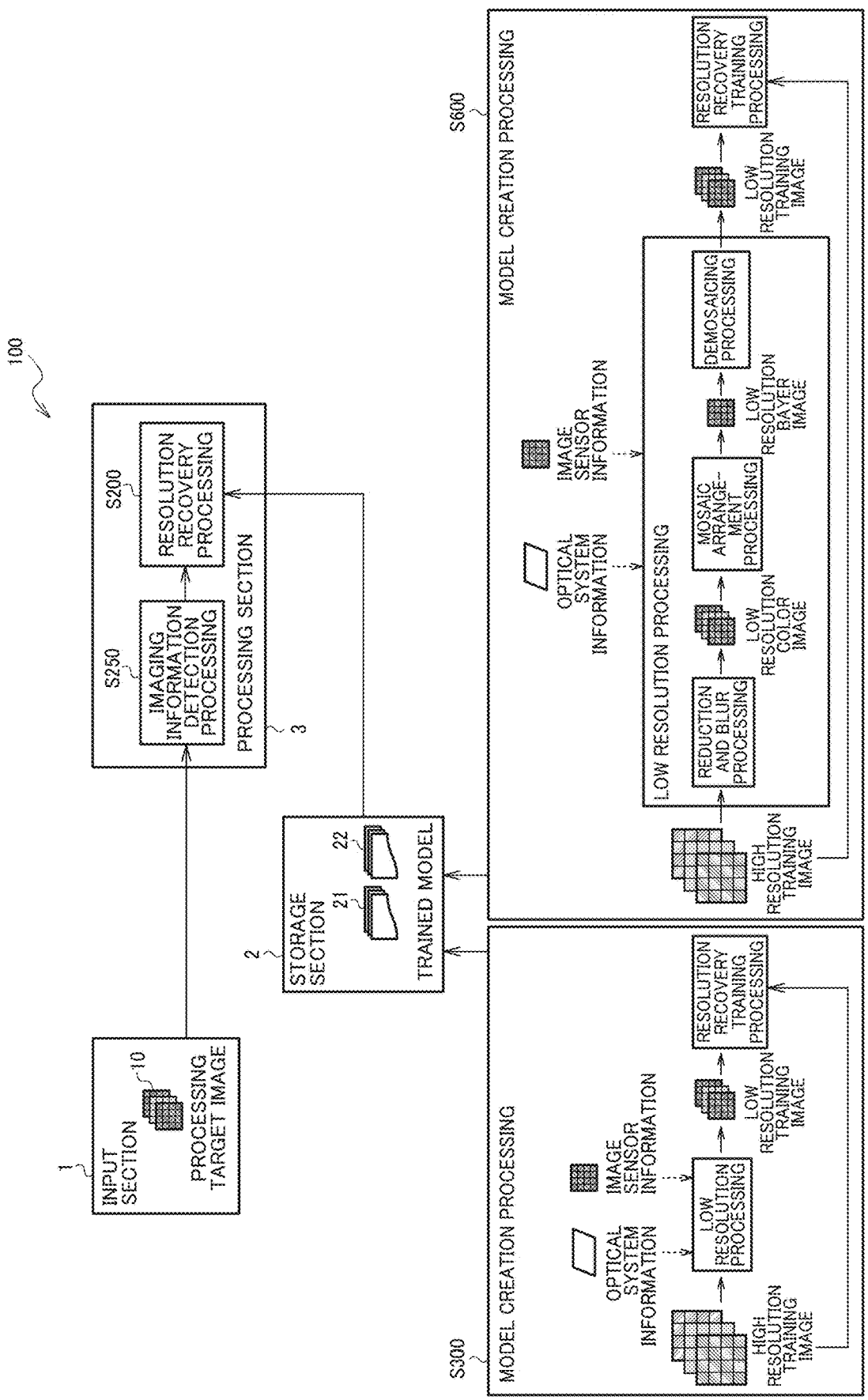
FIG. 9 illustrates a configuration example of an information processing system in accordance with a third embodiment and a processing flow of model creation processing.

FIG. 9 illustrates a configuration example of the information processing system 100 in accordance with the third embodiment and a processing flow of model creation processing S300 and S600. A configuration and processing of the input section 1 are similar to those of the first embodiment. In addition, the model creation processing S300 and S600 is similar to that in the first and second embodiments.

The storage section 2 stores a first trained model 21 and a second trained model 22. The first trained model 21 is generated by the model creation processing S300 described in the first embodiment. The second trained model 22 is generated by the model creation processing S600 described in the second embodiment.

Figure 10:
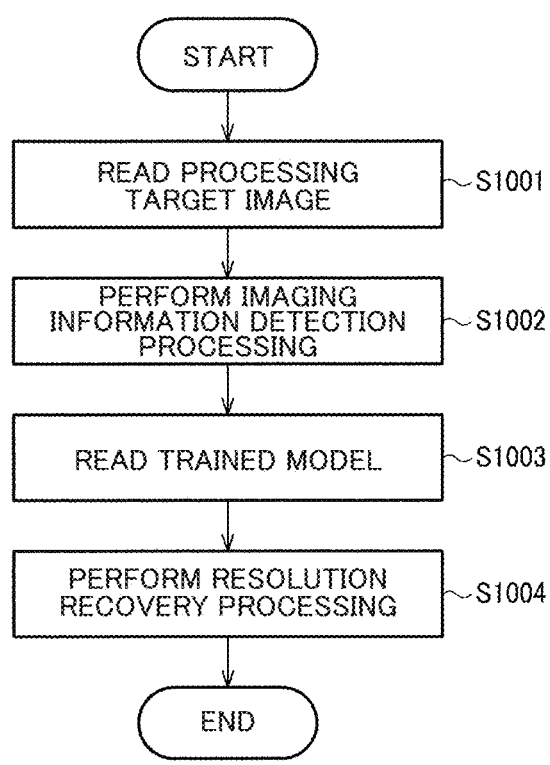
FIG. 10 illustrates a processing flow of imaging information detection processing and resolution recovery processing.

The processing section 3 performs imaging information detection processing S250 that detects an imaging method, and resolution recovery processing S200 that is processing of using a result of the detection to perform resolution recovery. FIG. 10 illustrates a processing flow of the imaging information detection processing S250 and the resolution recovery processing S200.

In step S1001, the processing section 3 reads the processing target image 10 from the input section 1. In step S1002, the processing section 3 detects imaging information from the processing target image 10, and determines an imaging method based on the imaging information. The imaging information is, for example, image information such as color distribution of the processing target image 10, a color shift amount in an edge portion in the field sequential method, and the number of pixels. The imaging method is the field sequential method or the simultaneous method. When the processing target image 10 is captured in the field sequential method, the processing target image 10 includes imaging information corresponding to the field sequential method. When the processing target image 10 is captured in the simultaneous method, the processing target image 10 includes imaging information corresponding to the simultaneous method.

A supplementary explanation is now given of the imaging method. Note that the following description is given using an example of a case of capturing a white image in RGB. In the field sequential method, the light source sequentially emits R light, G light, and B light. The imaging system includes the monochrome image sensor, captures an R image at a timing when the light source emits R light, captures a G image at a timing when the light source emits G light, and captures a B image at a timing when the light source emits B light. The images in three colors are combined into a color image. In the simultaneous method, the light source emits white light. The white light includes, for example, a continuous spectrum that covers a visible light range. The imaging system includes the Bayer-type image sensor, and captures an image in a Bayer array. The demosaicing processing is performed on the image in the Bayer array to generate the color image.

A supplementary explanation is now given of the imaging information. First, color distribution is described. As described above, a light source is different between the field sequential method and the simultaneous method. Thus, a tinge of the image, such as a tinge of red of the living body, is differently seen in an image. The processing section 3 uses a hue or the like to determine the tinge of the image, and thereby determines the imaging method. Subsequently, a color shift amount in an edge portion is described. As described above, since imaging timings of R, G, and B are different in the field sequential method, an object position is shifted among R, G, and B. The processing section 3 uses matching processing or the like to detect a color shift amount in the edge portion. In a case where the color shift amount is larger than a predetermined value, the processing section 3 determines that the imaging method is the field sequential method. Subsequently, the number of pixels is described. As described above, since the image sensor is different between the field sequential method and the simultaneous method, there is a case where the number of pixels of the captured image is different. The processing section 3 determines the imaging method from the number of pixels of the processing target image 10.

In step S1003, the processing section 3 reads out the trained model corresponding to the imaging method determined in step S1002 from the storage section 2. That is, when determining that the imaging method is the field sequential method, the processing section 3 reads out the first trained model 21 from the storage section 2. When determining that the imaging method is the simultaneous method, the processing section 3 reads out the second trained model 22 from the storage section 2.

In step S1004, the processing section 3 uses the trained model acquired in step S1003 to perform resolution recovery processing on the processing target image 10 acquired in step S1001, and generates the high resolution image.

In accordance with the present embodiment, the storage section 2 stores the first trained model 21, which is a trained model corresponding to the second imaging system, and the second trained model 22 corresponding to a third imaging system that performs imaging at a lower resolution than a resolution of the first imaging system. The input section 1 enters, to the processing section 3, a first processing target image captured through the second imaging system or a second processing target image captured through the third imaging system as the processing target image 10. The processing section 3 uses the first trained model 21 to perform resolution recovery on the first processing target image, and uses the second trained model to perform resolution recovery on the second processing target image.

With this processing, a trained model in accordance with the imaging system that captures the processing target image 10 is selected. This can implement a high-performance super resolution corresponding to a plurality of imaging systems. That is, a trained model having an appropriate recovery parameter in accordance with each imaging system is selected, whereby a high-performance super resolution can be implemented regardless of the imaging system.

Additionally, in the present embodiment, the processing section 3 detects a type of the imaging system that captures the processing target image 10 from the processing target image 10. When determining that the first processing target image is entered based on a result of the detection, the processing section 3 selects the first trained model 21. When determining that the second processing target image is entered based on a result of the detection, the processing section 3 selects the second trained model 22.

This enables determination of a type of the imaging system from the processing target image 10, and selection of a trained model corresponding to the type of the imaging system.

4. Fourth Embodiment

In a fourth embodiment, the information processing system is used as an endoscope system. In the endoscope system, various kinds of endoscopic scopes are detachably mounted. In the fourth embodiment, resolution recovery is performed in accordance with an endoscopic scope mounted on the endoscope system. Specifically, a type of an imaging system of the endoscopic scope is detected, and resolution recovery corresponding to a result of the detection is performed. A description will be given using an example of a case where an imaging method is different depending on the type of the imaging system, but a configuration is not limited thereto, and a resolution of the processing target image is only required to be different depending on the type of the imaging system. For example, the number of pixels, an optical system, or the like may be different depending on the type of the imaging system. Note that a description of a configuration and processing similar to those in the first to third embodiments is omitted.

Figure 11:
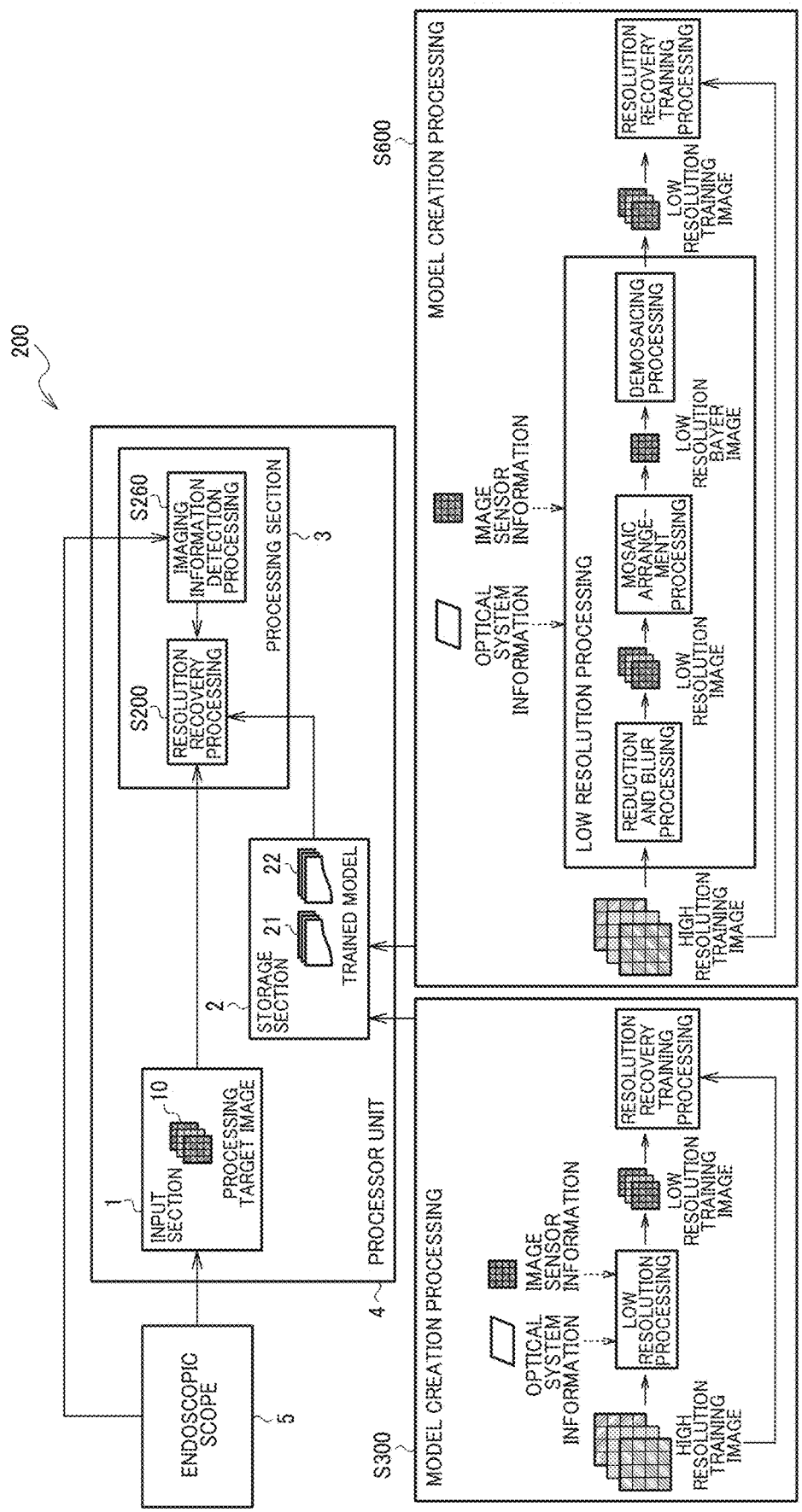
FIG. 11 illustrates a configuration example of an endoscope system in accordance with a fourth embodiment and a processing flow of model creation processing.

FIG. 11 illustrates a configuration example of an endoscope system 200 in accordance with the fourth embodiment and a processing flow of model creation processing S300 and S600. The endoscope system 200 includes a processor unit 4 and an endoscopic scope 5 that is connected to the processor unit 4. The processor unit 4 includes the input section 1, the storage section 2, and the processing section 3. The input section 1 is similar to that in the first embodiment, and the storage section 2 is similar to that in the third embodiment, and the model creation processing S300 and S600 is similar to that in the first and second embodiments.

Figure 12:
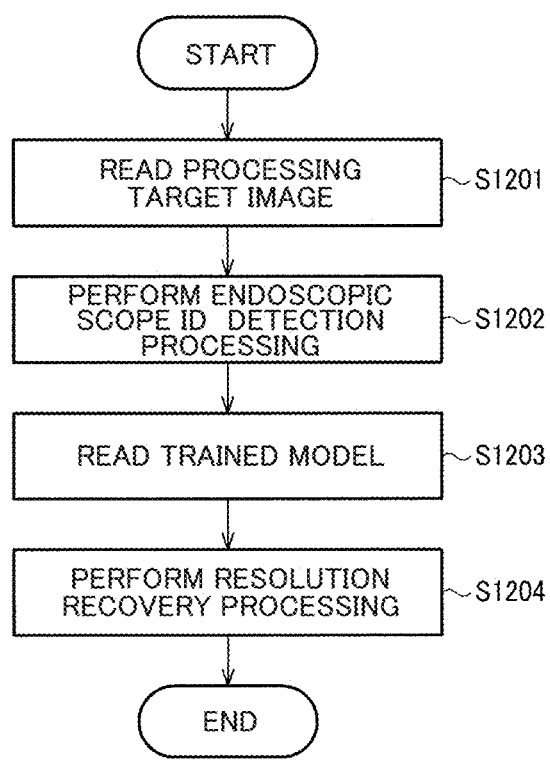
FIG. 12 illustrates a processing flow of imaging information detection processing and resolution recovery processing.

The processing section 3 performs imaging information detection processing S260 that detects an imaging method of the endoscopic scope 5 connected to the processor unit 4 and resolution recovery processing S200 that uses a result of the detection to perform resolution recovery. FIG. 12 illustrates a processing flow of the imaging information detection processing S260 and the resolution recovery processing S200.

In step S1201, the processing section 3 reads the processing target image 10 from the input section 1. In step S1202, the processing section 3 detects identification (ID) of the endoscopic scope 5. The ID includes optical system information of an imaging system included in the endoscopic scope 5 and imaging method information. In step S1203, the processing section 3 reads the trained model corresponding to the ID detected in step S1202 from the storage section 2. That is, in a case where the ID indicates the field sequential method, the processing section 3 reads out the first trained model 21 from the storage section 2, and, in a case where the ID indicates the simultaneous method, the processing section 3 reads out the second trained model 22 from the storage section 2. In step S1204, the processing section 3 uses the trained model acquired in step S1203 to perform resolution recovery processing on the processing target image 10 acquired in step S1201, and generates a high resolution image.

In accordance with the present embodiment, the processing section 3 detects ID information of the endoscopic scope 5 connected to the processor unit 4. When determining that the endoscopic scope 5 includes the second imaging system based on the ID information, the processing section 3 selects the first trained model 21. When determining that the endoscopic scope 5 includes the third imaging system based on the ID information, the processing section 3 selects the second trained model 22.

With this processing, a trained model in accordance with the ID information of the endoscopic scope is selected. This can implement a high-performance super resolution corresponding to a plurality of types of endoscopic scopes. That is, a trained model having an appropriate recovery parameter in accordance with each type of an endoscopic scope is selected, whereby high-performance super resolution can be implemented regardless of a type of the endoscopic scope.

5. Modification

Various kinds of modifications will be described below.

A first modification is now described. While least one of the optical system information or the image sensor information is used in the low resolution processing in the first to fourth embodiments, information of a light source may be additionally used. In the first modification, the low resolution processing is switched depending on the light source used when the processing target image is captured. Specifically, since the light source is different depending on an observation method, switching depending on the light source can be also said as switching depending on the observation method.

The observation method is also called as an observation mode. Examples of the observation method include white light imaging (WLI) that uses white illumination light and special light observation that uses special light, which is not white light. The following description will be given using an example of a case where the special light observation is narrow band imaging (NBI) that uses two types of narrow band light. The two types of narrow band light are narrow band light included in a wavelength band of blue light and narrow band light included in a wavelength band of green light. The image processing is different between the WLI and the NBI when a color image is generated from image signals output by the image sensor. For example, a content of the demosaicing processing or a parameter in the image processing is different.

Figure 13:
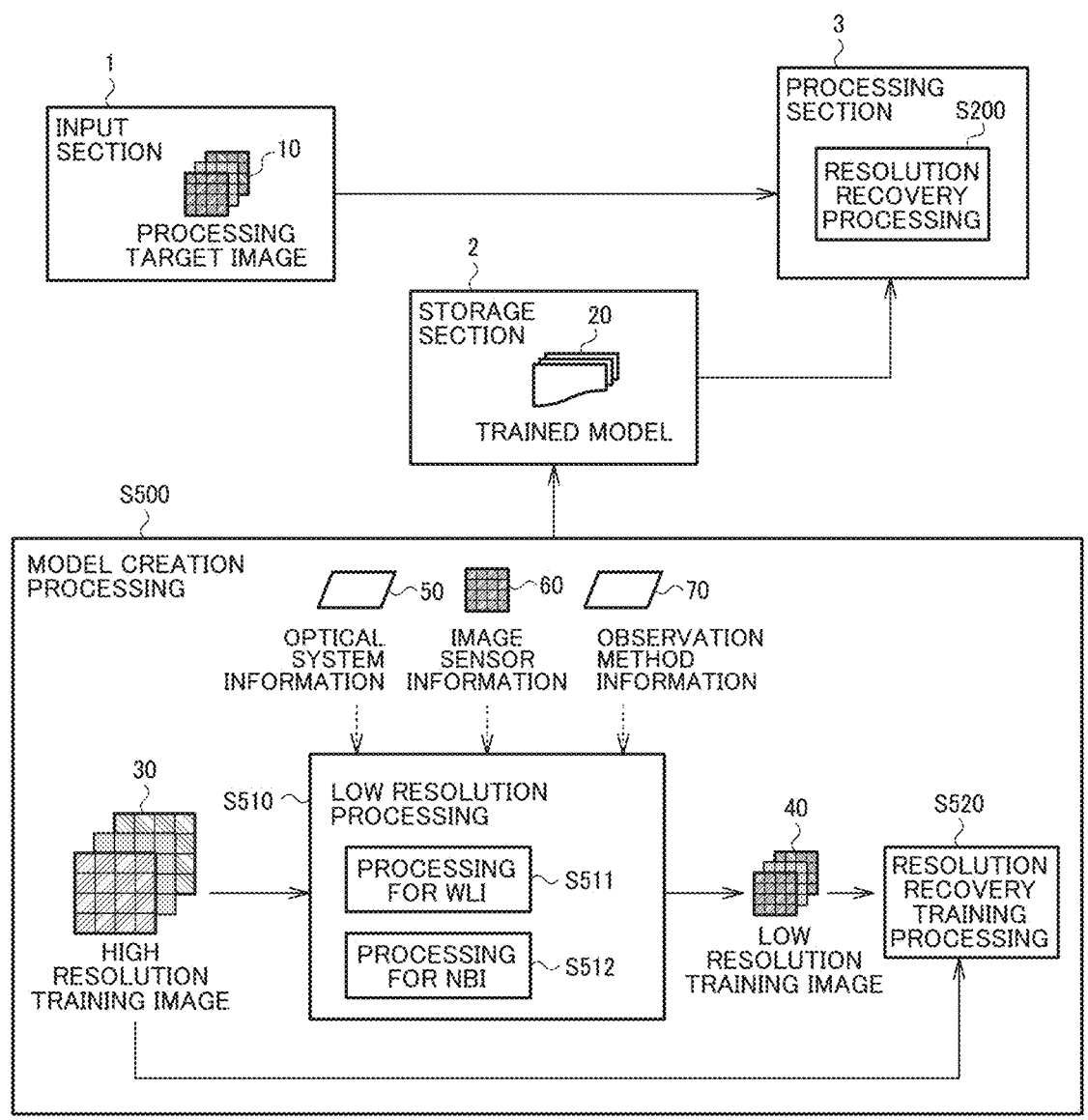
FIG. 13 illustrates a configuration example of an information processing system in accordance with a first modification and a processing flow of model creation processing.

FIG. 13 illustrates a configuration example of the information processing system 100 in accordance with a first modification and a processing flow of model creation processing S500.

In low resolution processing S510 of the model creation processing S500, the training processing section acquires observation method information 70, and switches processing depending on the observation method information 70. The observation method information 70 is information indicating an observation method used when the processing target image 10 is captured. In a case where the observation method information 70 indicates WLI, the training processing section selects processing for WLI S511. In a case where the observation method information indicates NBI, the training processing section selects processing for NBI S512. Each of the processing for WLI S511 and the processing for NBI S512 is processing for reducing the resolution of the high resolution training image 30 into the low resolution training image 40. For example, in the processing for WLI S511, the training processing section uses the G image to interpolate the R image and the B image in the demosaicing processing. On the other hand, in the processing for NBI S512, the training processing section independently interpolates the G image and the B image in the demosaicing processing.

In accordance with a first modification, the processing target image 10 is generated by image processing corresponding to the light source that is used when the first imaging system performs imaging. The low resolution processing S510 includes image processing corresponding to the light source (S511 and S512).

This enables implementation of high-performance super resolution processing regardless of an observation method. That is, since the image processing is different depending on the observation method, the sense of resolution of the processing target image also changes. In accordance with the first modification, switching the image processing in accordance with the observation method enables generation of the low resolution training image that has a sense of resolution that is equivalent to the sense of resolution of the processing target image. This can increase accuracy in super resolution.

A second modification is now described. In the second embodiment, the image processing to make the Bayer image the low resolution training image is the demosaicing processing, or the demosaicing processing and the noise reduction processing, but the image processing is not limited thereto. The image processing to make the Bayer image the low resolution training image may include various kinds of image processing such as correction of a defective pixel or edge enhancement processing.

A third modification is now described. In the first embodiment, to generate the low resolution training image in which the optical system information is reflected, the PSFs or the OTFs of the two optical systems are used to add the blur to the image, a method of addition of the blur is not limited thereto. The image captured through usage of the optical system of the first imaging system and the image captured through usage of the optical system of the second imaging system may be used to experimentally determine an amount of the blur that is added to the image. Specifically, a plurality of two-dimensional filters that approximates the blur with Gaussian or the like is generated. The plurality of two-dimensional filters approximates mutually different amounts of the blur. The plurality of two-dimensional filters is generated with respect to an image captured through usage of the optical system of the first imaging system, and a plurality of obtained images and an image captured through usage of the optical system of the second imaging system are compared. A two-dimensional filter that approximates an optimal amount of the blur is selected based on a result of the comparison.

The third modification enables low resolution processing that reflects optical system information in a simplified manner That is, in a case where the PSF or the OTF of the imaging system is not known, the two-dimensional filter such as Gaussian enables approximation of a resolution characteristic of the optical system.

Figure 14:
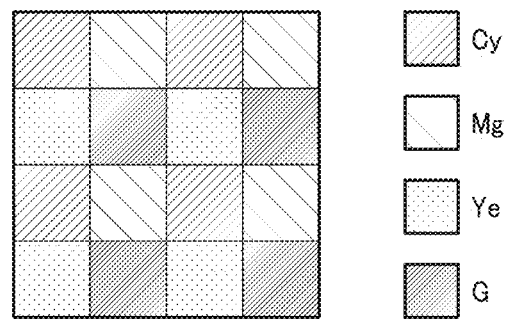
FIG. 14 illustrates an example of a complementary color-type image sensor.
Figure 15:
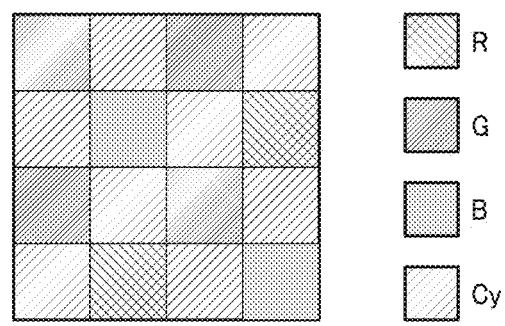
FIG. 15 illustrates an example of a mixed-type image sensor.

A fourth modification is now described. While the description has been given of the example in which the simultaneous-type image sensor is the Bayer-type image sensor in the second embodiment, the simultaneous-type image sensor is not limited thereto, and may be an image sensor having any color array. For example, the simultaneous-type image sensor may have a complementary color array illustrated in FIG. 14, or may have an array in which primary color pixels and complementary color pixels are mixed as illustrated in FIG. 15. In a complementary color-type image sensor illustrated in FIG. 14, a cyan (Cy) pixel, a magenta (Mg) pixel, a yellow (Ye) pixel, and a green (G) pixel are arranged in a unit of 2×2 pixels, and the unit is repeatedly arranged. In a mixed-type image sensor illustrated in FIG. 15, a red (R) pixel, the green (G) pixel, a blue (B) pixel, and the cyan (Cy) pixel are arranged in a unit of 2×2 pixels, and the unit is repeatedly arranged.

In consideration of the fourth modification, the simultaneous-type image sensor has, for example, the following configuration. For example, the simultaneous-type image sensor may include at least pixels in two colors out of pixels in four colors, i.e., the Cy pixel, the Mg pixel, the Ye pixel, and the G pixel provided with respective color filters in Cy, Mg, Ye, and G. Alternatively, the simultaneous-type image sensor may have a complementary color system array including pixels in four colors, i.e. the Cy pixel, the Mg pixel, the Ye pixel, and the G pixel provided with the respective color filters in Cy, Mg, Ye, and G. Still alternatively, the simultaneous-type image sensor may include at least pixels in two colors out of pixels in three colors, i.e., the R pixel, the G pixel, and the B pixel provided with respective three color filters in R, G, and B. Still alternatively, the simultaneous-type image sensor may have the Bayer array.

A fifth modification is now described. While the imaging information indicating the type of the imaging system is detected from the processing target image in the third embodiment, a method of detecting the imaging information is not limited thereto. For example, in a case where the user preliminarily grasps the imaging information of the processing target image, the user may enter the information to the information processing system 100.

A sixth modification is now described. In the second embodiment, mosaic arrangement is performed on the high resolution training image captured in the field sequential method to generate the low resolution Bayer image. Assume that the low resolution Bayer image is an image captured in the simultaneous method. As described above, since color shift occurs in the field sequential method but does not occur in the simultaneous method, it is not desirable to generate the low resolution Bayer image from an image of a scene where color shift frequently occurs in terms of accuracy of super resolution.

Figure 16:
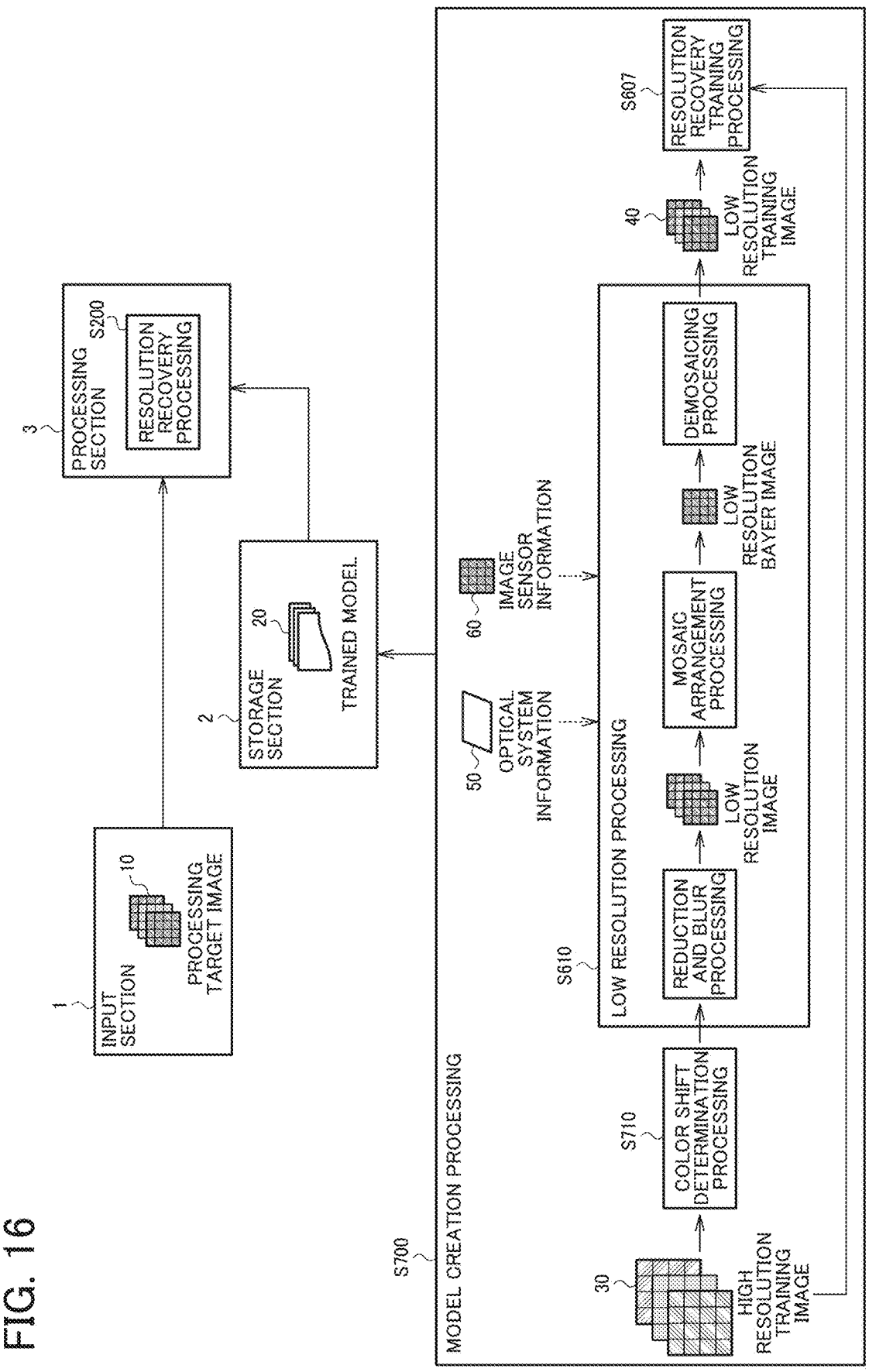
FIG. 16 illustrates a configuration example of an information processing system in accordance with a sixth modification and a processing flow of model creation processing.

FIG. 16 illustrates a configuration example of the information processing system 100 in accordance with the sixth modification and a processing flow of model creation processing S700. The configuration and operation of the information processing system 100 are similar to those of the second embodiment.

In the model creation processing S700, the training processing section performs color shift determination processing S710 on the high resolution training image 30. The training processing section performs the low resolution processing S610 on the high resolution training image 30 having a color shift amount that is smaller than a predetermined value to generate the low resolution training image 40. In the color shift determination processing S710, for example, the training processing section compares a coloring amount in a periphery of a saturated portion or the like in the image and a predetermined threshold.

In the sixth modification, in a case where light having a plurality of wavelength bands is sequentially emitted, the first imaging system causes the monochrome image sensor to perform imaging at a timing when light of each wavelength band is emitted, thereby acquires a plurality of images. The high resolution training image 30 is a field sequential image obtained by combining the plurality of images. The trained model 20 is trained through usage of the field sequential image (30) having a color shift amount that is equal to or less than a preset threshold in the field sequential image.

This enables execution of training of resolution recovery using only a scene with a small amount of color shift. This can implement high-performance super resolution processing on the image captured through the simultaneous-type low resolution image sensor while preventing the influence of the color shift.

A seventh modification is now described. The low resolution processing is performed on the high resolution training image 30 to output the low resolution training image 40 in the first embodiment, but known gray scale processing, in addition to the low resolution processing, may be performed on the high resolution training image 30 to output a monochrome low resolution training image.

Using the monochrome low resolution training image to perform resolution recovery training processing allows the trained model to, even if the processing target image 10 captured through the second imaging system is a monochrome image, not only resolution recover the processing target image 10, but also reproduce an actual tinge of the object in the processing target image 10.

6. Training Device and Endoscope System

Figure 17:
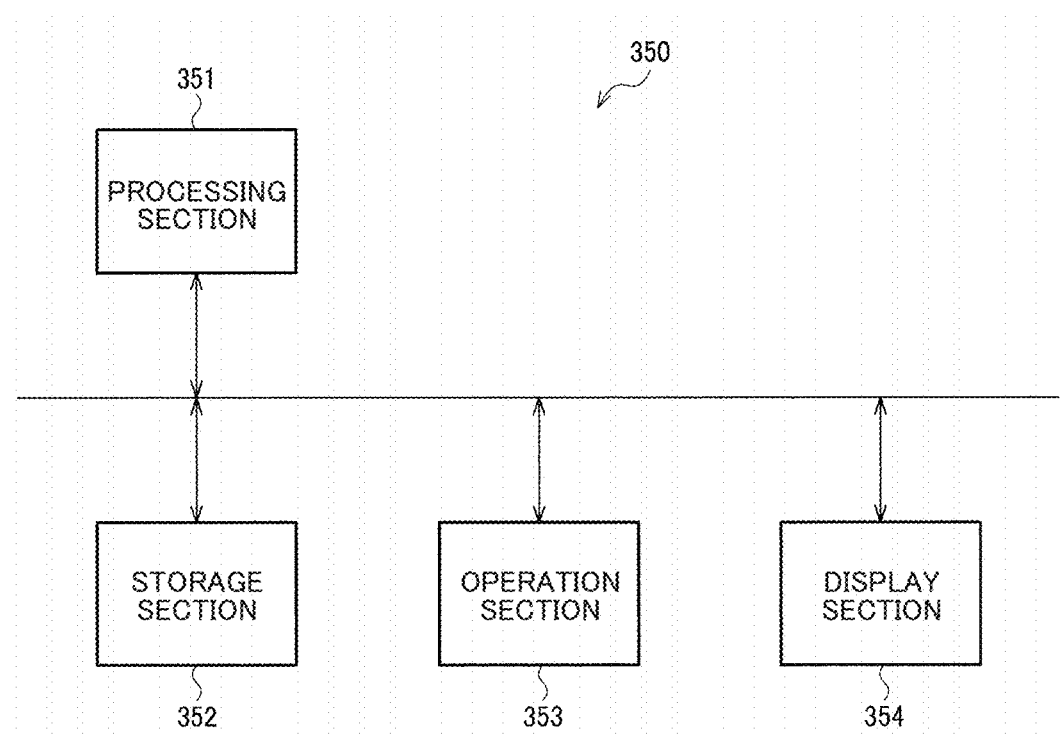
FIG. 17 illustrates a configuration example of a training device.

FIG. 17 illustrates a configuration example of a training device 350 that executes the above-mentioned model creation processing. The training device 350 includes a processing section 351, a storage section 352, an operation section 353, and a display section 354. For example, the training device 350 is an information processing device such as a personal computer (PC) and a server. The processing section 351 is a processor such as a CPU. The processing section 351 performs machine learning on a training model to generate a trained model. The storage section 352 is a storage device such as a semiconductor memory and a hard disk drive. The operation section 353 is an operation input device of various kinds, such as a mouse, a touch panel, and a keyboard. The display section 354 is a display device such as a liquid crystal display. Note that the training device 350 may be a cloud system in which a plurality of information processing devices connected to a network performs parallel processing. Alternatively, the information processing system 100 illustrated in FIG. 1 or the like may also serve as the training device. In this case, the processing section 3 and the storage section 2 also serve as the processing section 351 and storage section 352 of the training device 350, respectively.

The trained model generated by the training device 350 is stored in the storage section 2 of the information processing system 100. Note that the trained model may be stored in an information storage medium, which is a computer readable storage medium. The information storage medium can be implemented by, for example, an optical disk, a memory card, a hard disk drive (HDD), or a semiconductor memory. The semiconductor memory is, for example, a read-only memory (ROM). The information processing system 100 reads out a program and data stored in the information storage medium, and performs various kinds of processing of the present embodiment based on the program and the data. That is, the program and parameter for causing a computer to execute the trained model in accordance with the present embodiment are stored in the information storage medium. The computer is a device provided with an input device, a processing section, a storage section, and an output section. The program is a program for causing the computer to execute an inference algorithm of the trained model. The parameter is a parameter used for the inference algorithm, and is, for example, a weight coefficient assigned between connected nodes in a neural network. As the information storage medium, various kinds of computer-readable storage media can be assumed, such as an optical disk including a digital versatile disk (DVD) and a compact disk (CD), a magnetic optical disk, a hard disk, and a memory including a non-volatile memory and a random-access memory (RAM).

Figure 18:
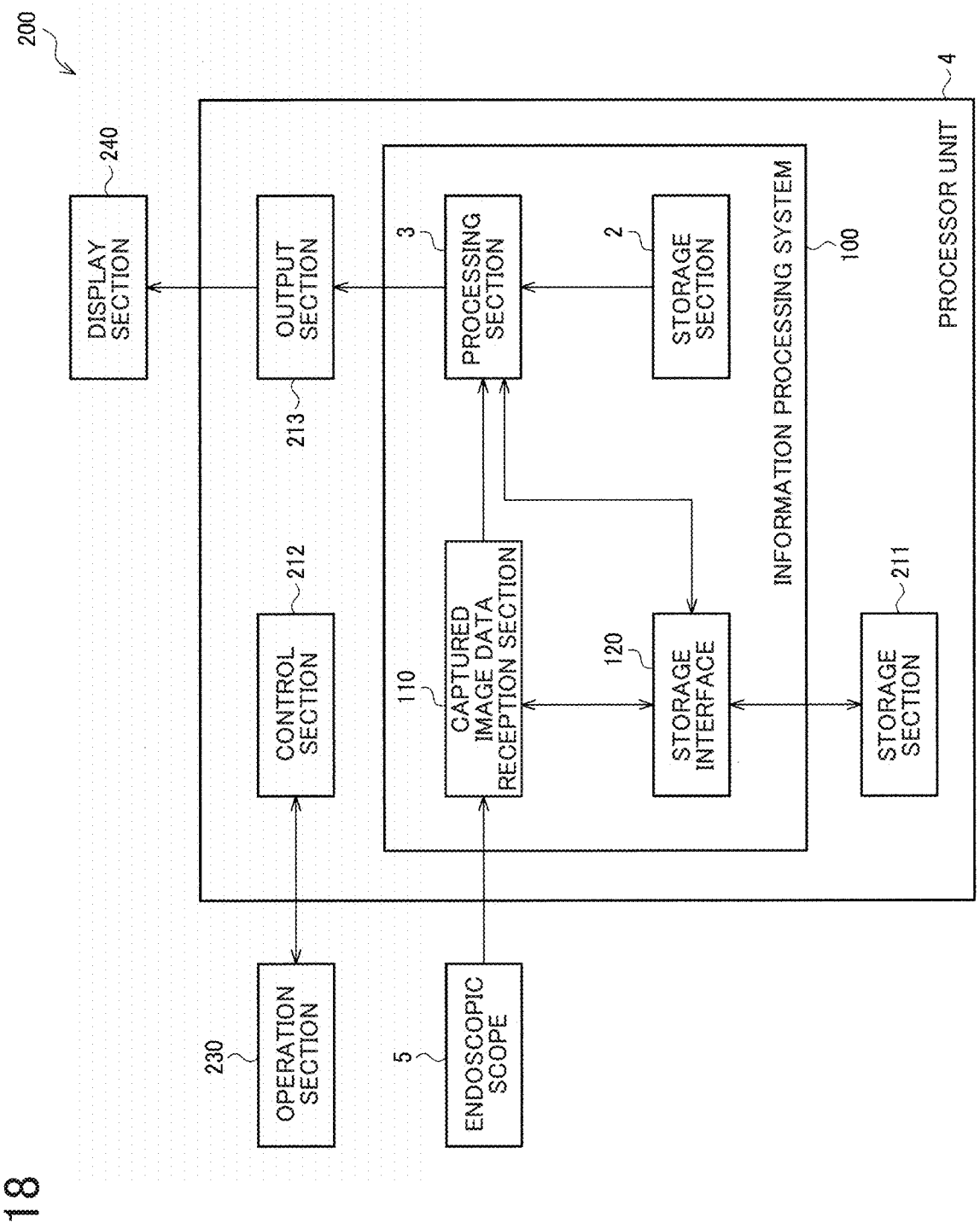
FIG. 18 illustrates a first configuration example of an endoscope system.

FIG. 18 illustrates a first configuration example of the endoscope system 200 including the information processing system 100. The endoscope system 200 includes the processor unit 4, the endoscopic scope 5, an operation section 230, and a display section 240.

An imaging device is arranged at a leading end portion of the endoscopic scope 5, and the leading end portion is inserted into a body cavity. The imaging device is the above-mentioned second imaging system. The imaging device captures an image of an abdominal cavity, and captured image data is transmitted from the endoscopic scope 5 to the processor unit 4.

The processor unit 4 is a device that performs various kinds of processing in the endoscope system 200. For example, the processor unit 4 performs control of the endoscope system 200, image processing, and the like. The processor unit 4 includes the information processing system 100, a storage section 211, a control section 212, and an output section 213.

The control section 212 performs control of each section of the endoscope system 200. For example, the control section 212 performs switching of a mode of the endoscope system 200, a zoom operation, switching of display, or the like, based on information entered from the operation section 230. The operation section 230 is a device for the user to operate the endoscope system 200. The operation section 230 is, for example, a button, a dial, a foot switch, a touch panel, or the like. Note that connection between the control section 212 and each section is not illustrated.

The storage section 211 records an image captured through the endoscopic scope 5. The storage section 211 is, for example, a semiconductor memory, a hard disk drive, an optical disk drive, or the like.

The information processing system 100 includes a captured image data reception section 110, a storage interface 120, the processing section 3, and the storage section 2. The captured image data reception section 110 receives captured image data from the endoscopic scope 5. The captured image data reception section 110 is, for example, a connector to which a cable of the endoscopic scope 5 is connected, an interface circuit that receives captured image data, or the like. The storage interface 120 is an interface for accessing the storage section 211. The storage interface 120 records image data received by the captured image data reception section 110 in the storage section 211. When replaying the recorded image data, the storage interface 120 reads out the image data from the storage section 211, and transmits the image data to the processing section 3. The processing section 3 performs resolution recovery processing with the image data from the captured image data reception section 110 or the storage interface 120 serving as the processing target image. The processing section 3 outputs the recovered high resolution image.

The input section 1 in the first to fourth embodiments corresponds to the captured image data reception section 110 or the storage interface 120 in FIG. 18.

The output section 213 is a display controller that controls image display on the display section 240, and causes the display section 240 to display the high resolution image output from the processing section 3. The display section 240 is a monitor that displays an image output from the output section 213, and is, for example, a display device such as a liquid crystal display and an organic electroluminescence (EL) display.

Note that the endoscope system 200 can include a light source, which is not illustrated. The light source generates illumination light. The endoscopic scope 5 includes a light guide that guides illumination light generated by the light source to the leading end portion of the scope, and an illumination lens that diffuses the guided illumination light.

Figure 19:
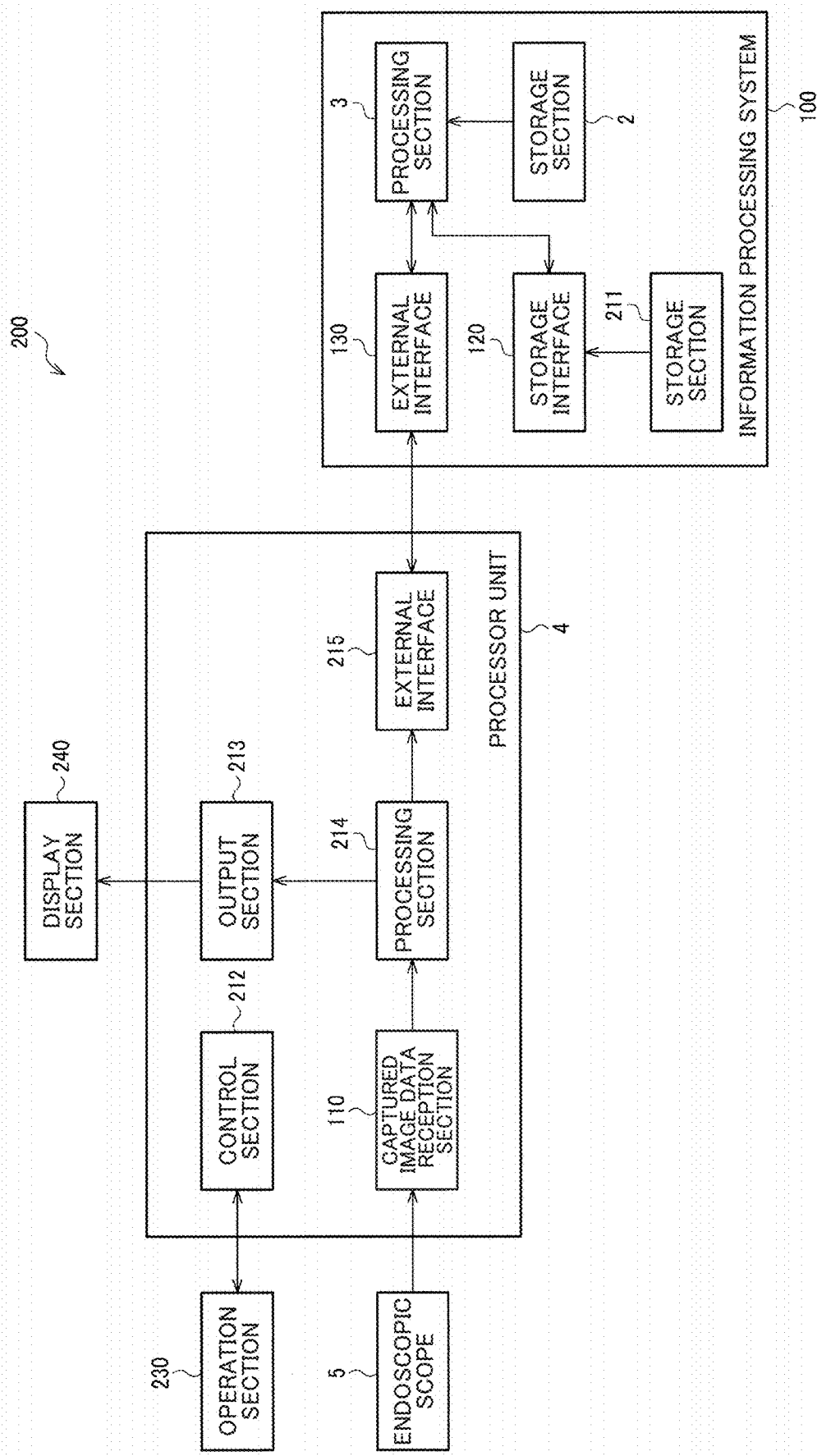
FIG. 19 illustrates a second configuration example of the endoscope system.

FIG. 19 illustrates a second configuration example of the endoscope system 200 including the information processing system 100. The endoscope system 200 includes the information processing system 100, the processor unit 4, the endoscopic scope 5, the operation section 230, and the display section 240.

In FIG. 19, the information processing system 100 is arranged outside the processor unit 4. The information processing system 100 and the processor unit 4 may be connected by device-to-device communication such as a universal serial bus (USB), or network communication such as a local area network (LAN) and a wide area network (WAN). The information processing system 100 includes one or more information processing devices. In a case where the information processing system 100 includes a plurality of information processing devices, the information processing system 100 may be a cloud system in which a plurality of PCs, a plurality of servers, or the like connected via the network performs parallel processing.

The processor unit 4 includes the captured image data reception section 110, the processing section 214, an external interface 215, the control section 212, and the output section 213. The processing section 214 transmits image data received by the captured image data reception section 110 to the information processing system 100 via the external interface 215. The information processing system 100 performs super resolution processing on the received image data to generate the high resolution image. The external interface 215 receives the high resolution image transmitted from the information processing system 100, and outputs the high resolution image to the processing section 214. The processing section 214 outputs the high resolution image to the output section 213, and the output section 213 causes the display section 240 to display the high resolution image.

The information processing system 100 includes an external interface 130, the processing section 3, the storage section 2, the storage interface 120, and the storage section 211. The external interface 130 receives the image data transmitted from the processor unit 4. The storage interface 120 and the storage section 211 are similar to those in the first configuration example. The processing section 3 performs resolution recovery processing with the image data from the external interface 130 or the storage interface 120 serving as the processing target image. The processing section 3 outputs the recovered high resolution image to the external interface 130, and the external interface 130 transmits the high resolution image to the processor unit 4.

The input section 1 in the first to fourth embodiments corresponds to the external interface 130 or the storage interface 120 in FIG. 19. The processing target image 10 in the first to fourth embodiments is not limited to endoscopic images, and can be medical images such as MRI images, X-ray images or CT images, or microscopic images, digital camera images.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An information processing system comprising:
a processor comprising hardware, the processor being configured to use a trained model and to receive a processing target image captured through a second imaging system that has a smaller number of pixels than pixels of a first imaging system including a first image sensor in a first imaging method, and that includes a second image sensor in a second imaging method different from the first imaging method, wherein:
the trained model is trained to resolution recover a low resolution training image to a high resolution training image,
the high resolution training image represents a high resolution image captured with a predetermined object through the first imaging system,
the low resolution training image is generated by low resolution processing performed on the high resolution training image,
the low resolution processing represents processing that generates a low resolution image as if captured with the predetermined object through the second imaging system,
in the low resolution processing, blur processing on the predetermined object that is optical system simulation processing that simulates a resolution characteristic of an optical system of the second imaging system on an image captured by the first imaging system based on optical system information of the first optical system and optical system information of the second optical system and reduction processing in which reduction ratio of the predetermined object is set based on image sensor information of the first image sensor and image sensor information of the second image sensor are performed, and
the processor is configured to use the trained model to resolution recover the processing target image to an image having a resolution at which the first imaging system performs imaging.

2. The information processing system as defined in claim 1, wherein the low resolution processing simulates the resolution characteristic based on a transfer function of the second imaging system in the optical system simulation processing.

3. The information processing system as defined in claim 2, wherein the low resolution processing performs, on the high resolution training image, deconvolution calculation of a point spread function (PSF) of the first imaging system and convolution calculation of a PSF of the second imaging system to simulate the resolution characteristic.

4. The information processing system as defined in claim 2, wherein the low resolution processing includes performing Fourier transformation on the high resolution training image, dividing a frequency characteristic of the high resolution training image serving as a result of the Fourier transformation by an optical transfer function (OTF) of the first imaging system, multiplying a result of the division by an OTF of the second imaging system, and performing inverse Fourier transformation on the calculated frequency characteristic to simulate the resolution characteristic.

5. The information processing system as defined in claim 1, wherein the second image sensor is an image sensor of an endoscope.

6. The information processing system as defined in claim 1, wherein:
in a case where light having a plurality of wavelength bands is sequentially emitted, the first imaging system causes a monochrome image sensor to perform imaging at a timing when light of each wavelength band is emitted, and thereby acquires a plurality of images,
the high resolution training image is a field sequential image obtained by combination of the plurality of images,
the second imaging system has a plurality of pixels having mutually different colors, and uses a synchronous-type image sensor in which one color is allocated to each pixel to acquire a mosaic image in which one color is allocated to each pixel,
the low resolution processing represents the blur processing and the reduction processing and that performs imaging method simulation processing on an image subjected to the reduction processing, and
the imaging method simulation processing represents processing that configures the mosaic image from the image subjected to the reduction processing and that performs demosaicing processing on the mosaic image to generate the low resolution training image.

7. The information processing system as defined in claim 6, wherein the imaging method simulation processing further includes noise reduction processing on the mosaic image.

8. The information processing system as defined in claim 6, wherein:
the processing target image is generated by image processing corresponding to a wavelength band of a light source that is used when the first imaging system performs imaging, and
the low resolution processing includes interpolating processing of an image corresponding to the wavelength band of the light source in the demosaicing processing.

9. The information processing system as defined in claim 1, wherein:
in a case where light having a plurality of wavelength bands is sequentially emitted, the first imaging system causes a monochrome image sensor to perform imaging at a timing when light of each wavelength band is emitted, and thereby acquires a plurality of images,
the high resolution training image is a field sequential image obtained by combination of the plurality of images, and
the trained model is trained by using the field sequential image having a color shift amount that is equal to or less than a present threshold in the field sequential image.

10. The information processing system as defined in claim 1, wherein the low resolution training image is generated by the low resolution processing and gray scale processing performed on the high resolution training image.

11. The information processing system as defined in claim 1, wherein:
a storage device stores a first trained model that is the trained model corresponding to the second imaging system, and a second trained model corresponding to a third imaging system that performs imaging at a lower resolution than a resolution at which the first imaging system performs imaging,
the processor is configured to receive, a first processing target image captured through the second imaging system or a second processing target image captured through the third imaging system as the processing target image, and
the processor is configured to use the first trained model to resolution recover the first processing target image, and use the second trained model to resolution recover the second processing target image.

12. The information processing system as defined in claim 11, wherein:
the processor is configured to detect a type of an imaging system that captures the processing target image from the processing target image, and
when determining that the first processing target image is entered based on a result of the detection, the processor is configured to select the first trained model, and when determining that the second processing target image is entered based on the result of the detection, the processor is configured to select the second trained model.

13. An endoscope system comprising:
the information processing system as defined in claim 1; and
an endoscope configured to capture the processing target image, and to transmit the processing target image to the information processing system.

14. A non-transitory computer-readable storage medium that stores a program that causes using a computer to use a trained model and to receive a processing target image captured through a second imaging system that has a smaller number of pixels than pixels of a first imaging system including a first image sensor in a first imaging method, and that includes a second image sensor in a second imaging method different from the first imaging method, wherein:
the trained model is trained to resolution recover a low resolution training image to a high resolution training image,
the high resolution training image represents a high resolution image captured with a predetermined object through the first imaging system,
the low resolution training image is generated by low resolution processing performed on the high resolution training image,
the low resolution processing represents processing that generates a low resolution image as if captured with the predetermined object through the second imaging system,
in the low resolution processing, blur processing on the predetermined object that is optical system simulation processing that simulates a resolution characteristic of an optical system of the second imaging system on an image captured by the first imaging system based on optical system information of the first optical system and optical system information of the second optical system and reduction processing in which reduction ratio of the predetermined object is set based on image sensor information of the first image sensor and image sensor information of the second image sensor are performed, and the program causes the computer to use the trained model to resolution recover the processing target image to an image having a resolution at which the first imaging system performs imaging.

15. The information processing system as defined in claim 1, wherein the blur processing is a processing that performs deconvolution of a point spread function of the first imaging system on the high resolution training image and performs convolution of a point spread function of the second imaging system on the result of the deconvolution of the point spread function of the first imaging system.

16. The information processing system as defined in claim 1, wherein the blur processing is a processing that performs fast fourier transform on the high resolution training image, divides the result of the fast fourier transform by an optical transfer function of the first imaging system, multiplies the result of the division by an optical transfer function of the second imaging system, and performs reverse fast fourier transform on the result of multiplication.

* * * * *